United States Patent
Yeo et al.

(10) Patent No.: US 12,268,551 B2
(45) Date of Patent: Apr. 8, 2025

(54) APPARATUS AND METHOD FOR FETAL INTELLIGENT NAVIGATION ECHOCARDIOGRAPHY

(71) Applicants: Wayne State University, Detroit, MI (US); The United States of America, as represented by the Secretary, Department of Health and Human Services, Bethesda, MD (US); Gustavo Eduardo Abella, Buenos Aires (AR); Ricardo Enrique Gayoso, Buenos Aires (AR)

(72) Inventors: Lami Yeo, Detroit, MI (US); Roberto Romero, Grosse Point, MI (US); Gustavo Eduardo Abella, Buenos Aires (AR); Ricardo Enrique Gayoso, Buenos Aires (AR)

(73) Assignees: WAYNE STATE UNIVERSITY, Detroit, MI (US); THE U.S.A., AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 314 days.

(21) Appl. No.: 17/526,798

(22) Filed: Nov. 15, 2021

(65) Prior Publication Data
US 2022/0142609 A1 May 12, 2022

Related U.S. Application Data

(63) Continuation of application No. 14/422,335, filed as application No. PCT/US2013/058661 on Sep. 8, 2013, now abandoned.
(Continued)

(51) Int. Cl.
A61B 8/08 (2006.01)
A61B 8/00 (2006.01)
A61B 8/14 (2006.01)

(52) U.S. Cl.
CPC .......... *A61B 8/0866* (2013.01); *A61B 8/0883* (2013.01); *A61B 8/14* (2013.01);
(Continued)

(58) Field of Classification Search
None
See application file for complete search history.

(56) References Cited

U.S. PATENT DOCUMENTS 5,279,576 A 1/1994 Loo et al.
6,599,273 B1 7/2003 Lopez
(Continued)

FOREIGN PATENT DOCUMENTS

WO 2011029466 A1 3/2011

OTHER PUBLICATIONS

Gonçalves, L. F., Romero, R., Espinoza, J., Lee, W., Treadwell, M., Chintala, K., . . . & Chaiworapongsa, T. (2004). Four-dimensional ultrasonography of the fetal heart using color Doppler spatiotemporal image correlation. Journal of ultrasound in medicine, 23(4), 473-481. (Year: 2004).*

(Continued)

*Primary Examiner* — Jason M Ip
*Assistant Examiner* — Renee C Langhals
(74) *Attorney, Agent, or Firm* — Fishman Stewart PLLC

(57) ABSTRACT

A method and apparatus of examining fetal hearts includes obtaining ultrasound data of a fetal heart to generate fetal heart images, displaying different marked sample images of a fetal heart and at respective cardiac phases, each marking a different feature of a fetal heart at a respective marked location, and sequentially presenting one of the different
(Continued)

marked sample images to a user along with one of the fetal heart images that is a similar view. As each of the different marked sample images is sequentially presented, a user is prompted to mark the different feature in a respective fetal heart image based on its marked location to create a plurality of marked fetal heart images, and a geometric model of the heart is generated based on the marked fetal heart images, from which fetal echocardiography views can be extracted. The fetal echocardiography views of the fetal heart are displayed.

33 Claims, 18 Drawing Sheets

Related U.S. Application Data

(60) Provisional application No. 61/698,569, filed on Sep. 8, 2012.

(52) U.S. Cl.
CPC .............. *A61B 8/461* (2013.01); *A61B 8/466* (2013.01); *A61B 8/5223* (2013.01); *A61B 8/54* (2013.01); *A61B 8/483* (2013.01)

(56) References Cited

U.S. PATENT DOCUMENTS

| | | | |
|---|---|---|---|
| 8,083,678 | B2 | 12/2011 | Abuhamad |
| 2002/0038093 | A1 | 3/2002 | Potse et al. |
| 2003/0153823 | A1 | 8/2003 | Geiser et al. |
| 2004/0097805 | A1 | 5/2004 | Verard et al. |
| 2005/0004465 | A1 | 1/2005 | Abuhamad |
| 2005/0251036 | A1 | 11/2005 | Abuhamad |
| 2006/0064017 | A1 | 3/2006 | Krishnan et al. |
| 2008/0089571 | A1 | 4/2008 | Kurita |
| 2011/0040183 | A1 | 2/2011 | Yoshida |
| 2011/0201935 | A1* | 8/2011 | Collet-Billon ....... A61B 8/0866 600/443 |
| 2011/0210734 | A1 | 9/2011 | Darrow et al. |
| 2012/0063656 | A1 | 3/2012 | Jao et al. |
| 2012/0253170 | A1* | 10/2012 | Kim .................. G06T 7/12 600/410 |
| 2013/0281854 | A1 | 10/2013 | Stuebe et al. |
| 2013/0345563 | A1* | 12/2013 | Stuebe ................ A61B 5/316 600/440 |

OTHER PUBLICATIONS

Jantarasaengaram, S., & Vairojanavong, K. (2010). Eleven fetal echocardiographic planes using 4-dimensional ultrasound with spatio-temporal image correlation (STIC): a logical approach to fetal heart volume analysis. Cardiovascular Ultrasound, 8(1), 1-8. (Year: 2010).*

Yagel et al., "3D and 4D ultrasound in fetal cardiac scanning: a new look at the fetal heart," Ultrasound Obstet Gynecol (2007) 29: 81-95.

Jantarasaengaram et al., "Eleven fetal echocardiographic planes using 4-dimensional ultrasound with spatio-temporal image correlation (STIC): a logical approach to fetal heart volume analysis," Cardiovascular Ultrasound (2010) 8 (41): 1-10.

International Search Report (Form PCT/ISA/210) dated Jan. 16, 2014 for corresponding International App. No. PCT/US2013/058661.

Written Opinion (Form PCT/ISA/237) dated Jan. 16, 2014 for corresponding International App. No. PCT/US2013/058661.

EA Junior et al., "Spatio-Temporal Image Correlation (STIC): A New Technique for Fetal Heart Evaluation," Radiol Bras, vol. 39, No. 5, pp. 373-377.

L.F. Goncalves et al., "Four-Dimensional Ultrasonography of the Fetal Heart Using Color Doppler Spatiotemporal Image Correlation," 2004, J Ultrasound Med, vol. 23, iss. 4, pp. 473-481.

* cited by examiner

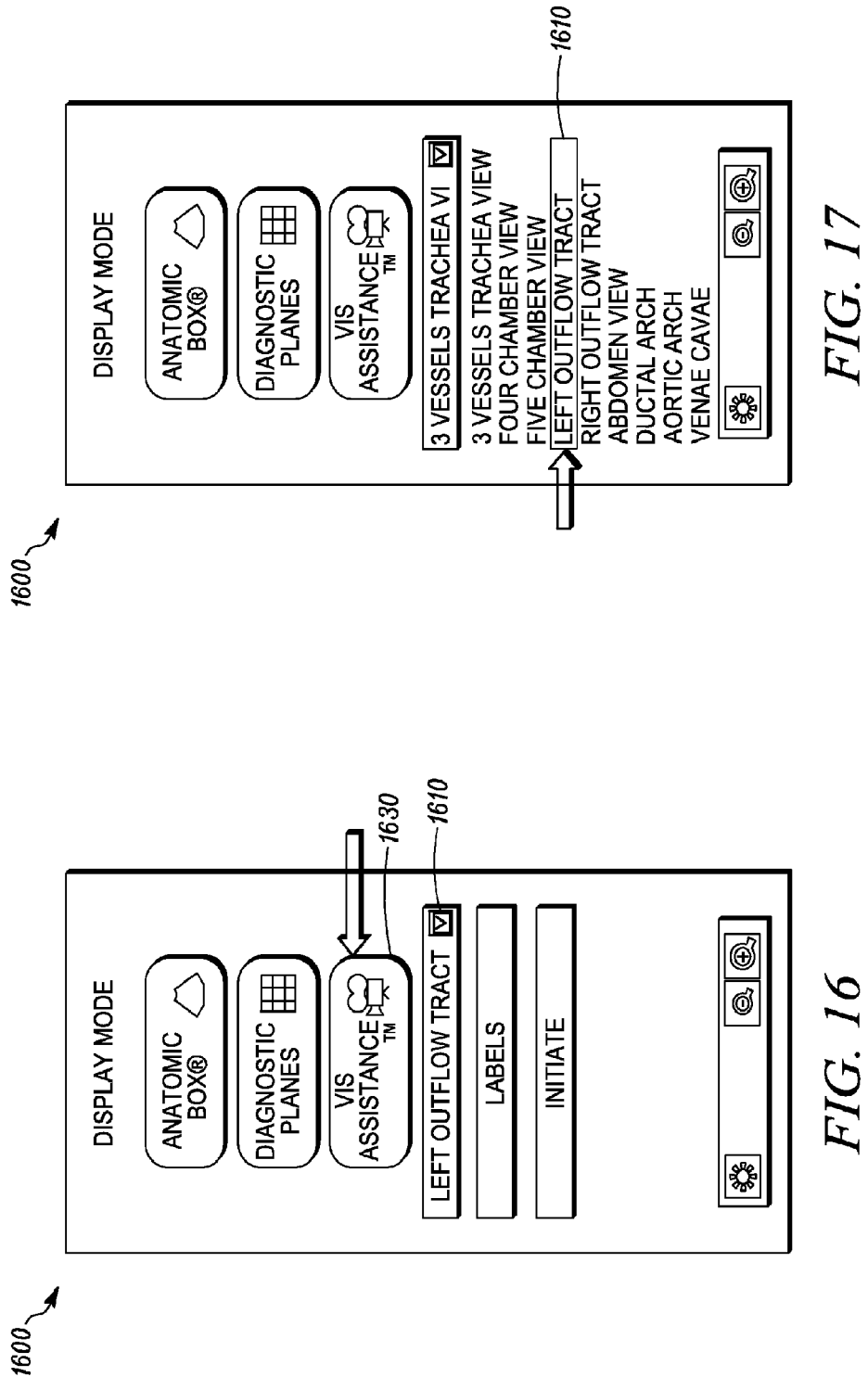

APPARATUS AND METHOD FOR FETAL INTELLIGENT NAVIGATION ECHOCARDIOGRAPHY

CROSS-REFERENCE TO RELATED APPLICATIONS

This application is a Continuation application of and claims priority to U.S. patent application Ser. No. 14/422,335, filed Feb. 18, 2015, which is a national phase application of and claims priority to International Patent Application No. PCT/US2013/058661, filed Sep. 8, 2013, which claims the benefit of U.S. Provisional Patent Application No. 61/698,569, filed Sep. 8, 2012, the contents of which is hereby incorporated by reference in their entirety.

BACKGROUND OF THE INVENTION

Congenital anomalies have become the leading cause of infant mortality in Caucasians in the United States. Congenital heart disease (CHD) is the most frequent of all congenital anomalies by organ system. However, the prenatal diagnosis of congenital heart anomalies is difficult and poor due to the complex structure of the organ and its small size. Yet, the prenatal diagnosis of CHD improves the likelihood of survival and reduces morbidity. Ultrasound examination of the fetus is the only method of screening for CHD prenatally. Pregnant women and their families expect that their unborn child will be evaluated to ensure that it is normal, and prenatal diagnosis of congenital anomalies has become an integral part of prenatal care. However, the reassurance currently being provided to most pregnant women in the U.S. about the normality of the fetal heart is misleading, because most cardiac examinations provided in practice are incomplete and inadequate due to the inability to obtain all cardiac planes required to adequately examine the fetal heart and diagnose anomalies.

There are many cardiac examinations that can be conducted. One such examination is spatiotemporal image correlation ("STIC"). Once a volume of the fetal heart is acquired using STIC, the challenge for the operator is to extract and generate standard cardiac diagnostic planes that will provide clinically relevant information. However, there are a large number of planes contained within the volume dataset, and an operator can easily get "lost" trying to obtain the standard planes to determine whether a fetal heart is normal or not.

SUMMARY OF THE INVENTION

Described is an apparatus and method for fetal intelligent navigation echocardiography (FINE). Use of this apparatus and method allows for visualization of standard fetal echocardiography views from dataset volumes obtained with spatiotemporal image correlation (STIC).

A method and apparatus employing the method demonstrates: 1) nine fetal cardiac diagnostic planes; and 2) spontaneous navigation of anatomy surrounding each of the nine diagnostic planes by way of a Virtual Intelligent Sonographer Assistance, also known as VIS-Assistance. After seven anatomical structures in the fetal heart are marked by the user, the following echocardiography views are automatically generated: 1) three-vessels and trachea; 2) four-chamber; 3) five-chamber; 4) left ventricular outflow tract; 5) short axis view of great vessels/right ventricular outflow tract; 6) abdomen/stomach; 7) ductal arch; 8) aortic arch; and 9) superior and inferior vena cava. The FINE method was tested in a separate set of 50 STIC volumes of normal hearts (18.6-37.2 weeks of gestation), and visualization rates for standard fetal echocardiography views using diagnostic planes and/or VIS-Assistance were calculated. In addition, to determine whether the method could identify abnormal anatomy, we tested the method in 4 cases with proven congenital heart defects (coarctation of aorta (n=1), tetralogy of Fallot, transposition of great vessels, and pulmonary atresia with intact ventricular septum).

In normal cases, the FINE method and apparatus was able to generate nine fetal echocardiography views using: 1) diagnostic planes in 78%-100%; 2) VIS-Assistance in 98-100% of cases; and 3) combination of diagnostic planes and/or VIS-Assistance in 98-100%. In the 4 abnormal cases, the FINE method demonstrated evidence of abnormal anatomy of the fetal heart in all cases. Therefore, the FINE method and apparatus can be used to visualize nine standard fetal echocardiography views in normal hearts by applying "intelligent navigation" technology to STIC volume datasets. The FINE method simplifies examination of the fetal heart considerably and reduces operator dependency. The appearance of abnormal views using diagnostic planes or VIS-Assistance should raise the index of suspicion for congenital heart disease.

BRIEF DESCRIPTION OF THE DRAWINGS

FIG. 16 is an image showing the prompt for selecting VIS-Assistance, according to an example embodiment.

FIG. 17 is an image showing the drop down menu for selecting VIS-Assistance for a particular diagnostic plane, according to an example embodiment.

INTRODUCTION

Figure 1A:
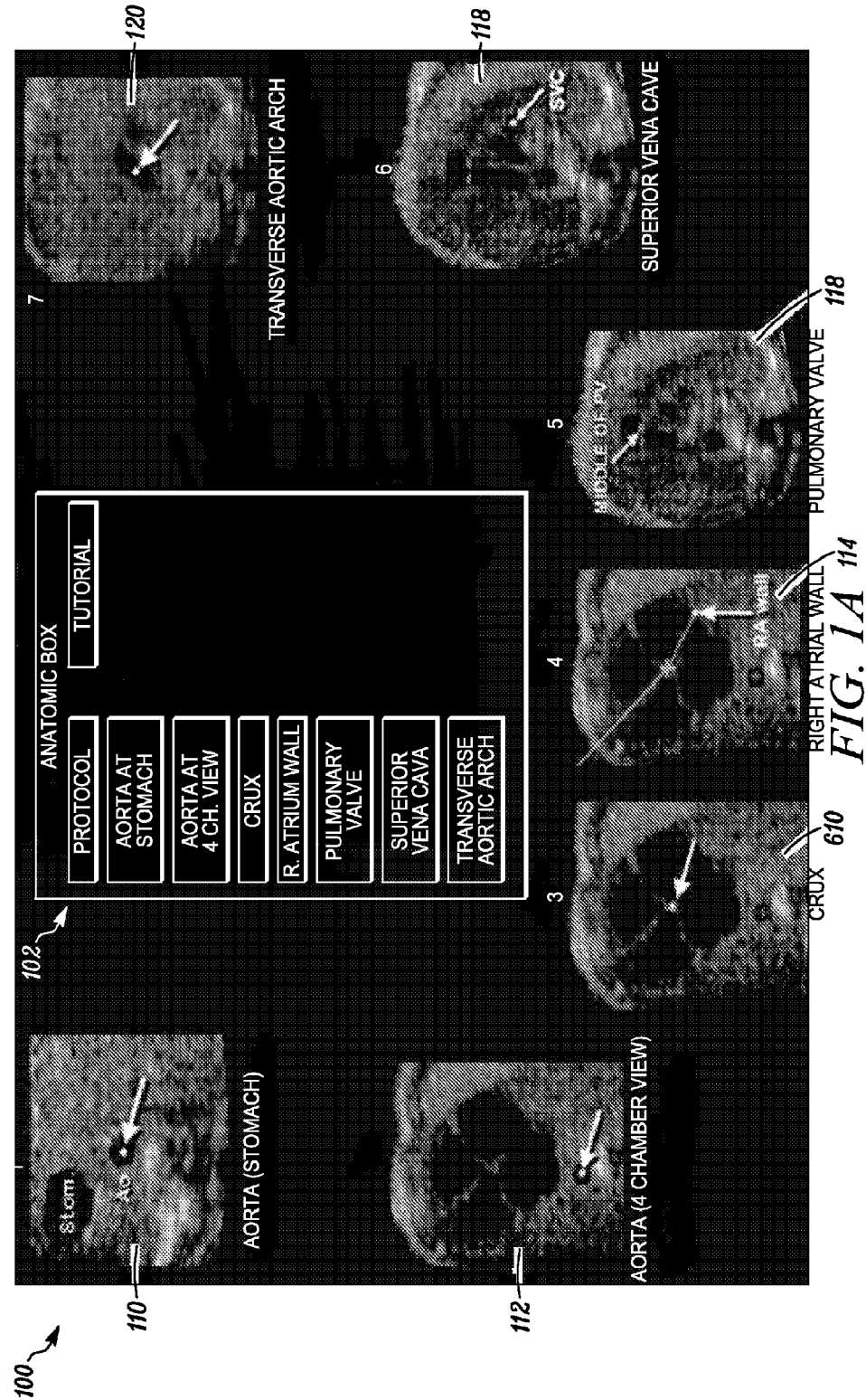
FIG. 1A is a display of the various anatomical structures, as marked, within the fetal heart volume data as captured, according to an example embodiment.

Congenital heart disease is the leading organ-specific birth defect, and is the number one cause of infant mortality from congenital malformations. More than half of infants affected with congenital heart disease are born to mothers without any previously known risk factors, and hence, the impetus to include a comprehensive examination of the fetal heart in all pregnancies. However, even in recent years, the prenatal diagnosis of congenital heart disease has remained challenging; the sensitivity has ranged from 15-39%. Some investigators have reported no secular improvement in sensitivity over a 10 year period. Indeed, despite almost universal access to sonographic screening during pregnancy, only 28% of major congenital heart defects have been detected prenatally. The failure of prenatal diagnosis can have adverse consequences for the neonate and have medicolegal implications.

The difficulties in prenatal diagnosis are generally attributed to the complex anatomy of the heart, its small size, motion, the importance of fetal position for an adequate examination, and the skills and experience required to accurately diagnose congenital heart disease. Frequently, examination of the fetal heart does not include all the standard recommended views (e.g. four-chamber, left and right ventricular outflow tracts, three-vessels and trachea).

Four-dimensional (4D) sonography with spatiotemporal image correlation (STIC) technology allows the acquisition of a volume dataset from the fetal heart, and displays a cine-loop of a complete single cardiac cycle in motion. A growing body of evidence suggests that 4D sonography with STIC facilitates examination of the fetal heart.

Spatio-temporal image correlation (STIC) can be used for clinical assessment of the fetal heart. The acquisition is performed in two steps: first, images are acquired by a single, automatic volume sweep. Second, the system analyzes the image data according to their spatial and temporal domain and processes an online dynamic 3D image sequence that is displayed in a multiplanar reformatted cross-sectional display and/or a surface rendered display. An operator can navigate within the heart, re-slice, and produce all of the standard image planes necessary for a comprehensive diagnosis. However, extracting and displaying the recommended diagnostic planes from the cardiac volume dataset (such as STIC) that can be dissected in many ways (i.e. planes) is difficult, operator dependent, and is time consuming Planes and cardiac structures may be difficult to recognize, particularly when the anatomy is abnormal.

Discussed below are various embodiments of methods, based upon STIC, for assisting users in systematically and efficiently interrogating cardiac volume datasets to allow the display of cardiac diagnostic planes. The method, described herein, namely, Fetal Intelligent Navigation Echocardiography (FINE) interrogates a STIC volume dataset using "intelligent navigation," which allows the determination of situs, and the automatic display of nine fetal echocardiography views required to diagnose most cardiac defects. The potential value of the FINE method is also illustrated in 4 cases with congenital heart defects.

Figure 5:
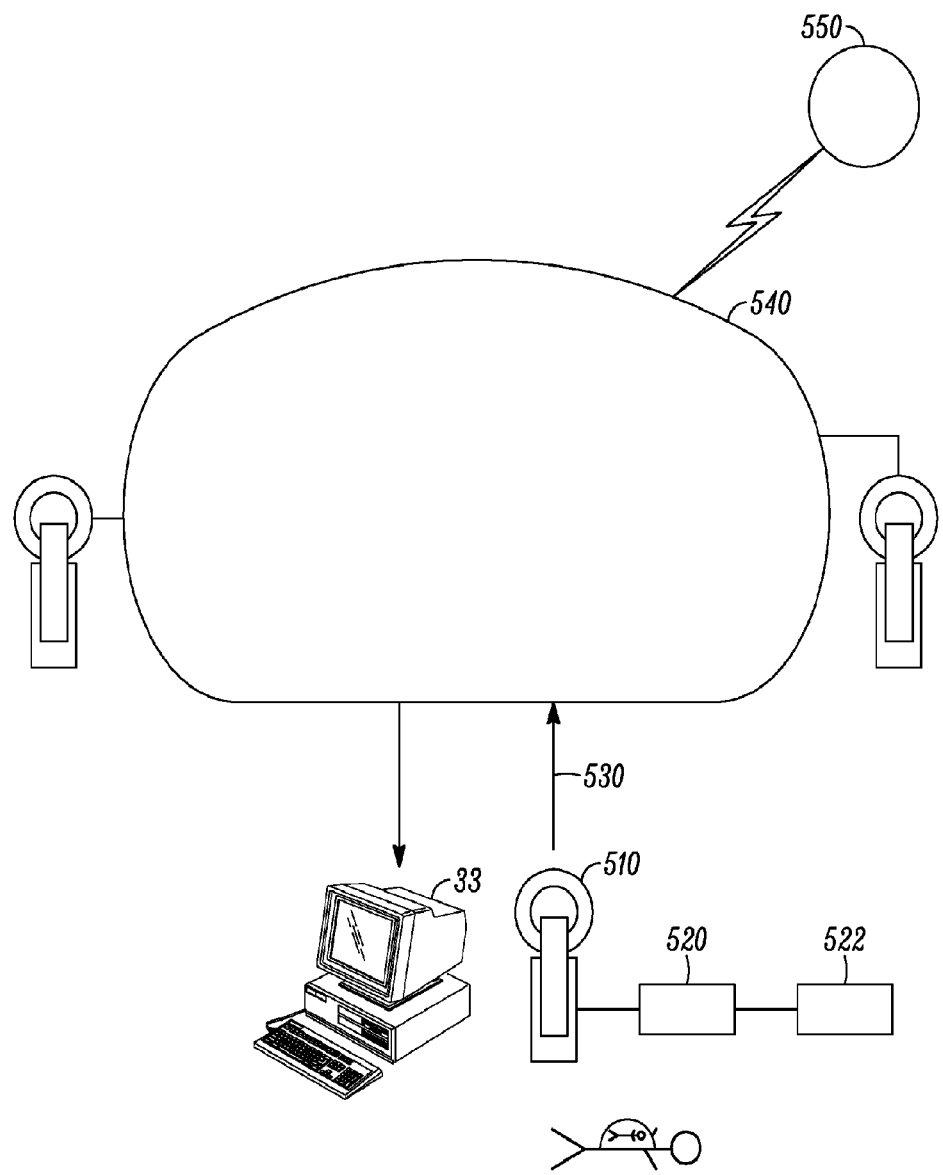
FIG. 5 is a schematic drawing of a system that captures and manipulates images, according to an example embodiment.

FIG. 5 is a schematic drawing of a system 500 that captures and manipulates images, according to an example embodiment. The system 500 includes an image capture device 510 capable of capturing data related to an image of various body parts of a patient. The system 500 also includes a processor 520 and memory 522 for processing the data obtained from the image capture device 510 and converting the data to useful information such as useful images. In some embodiments, the processor 520 can be a graphical processor or a graphical processing unit, which is adapted to efficiently handle the data obtained and convert it to useful information, such as images. The processor 520 can also convert the image data and information into various formats, such as DICOM or similar information. The system 500 can also include an interface 530 to a network 540, such as an inter-hospital network, and inter-clinic network, a wide area network, a phone network, the internet, or the like. The interface 530 may not provide a direct interface to some networks. For example, the interface 530, in one embodiment, is to an inter-hospital network. The inter-hospital network can have a link to the internet. As a result, the interface 530 can connect to the internet 550 or other network via the inter-hospital network. It should be noted that the image capture device 510 can be used to perform a number of modalities. In the discussion that follows, the modality discussed is spatio-temporal image correlation. In one embodiment, the image capture device 510 is an ultrasound machine, and STIC is one of the modalities the ultrasound machine can do. The system 500, as shown, is taking an image of a fetal heart.

As an overview, the imaging system 500 includes a processor that executes an instruction set that causes the computing system to perform operations includes obtaining dataset volumes of a heart, placing markers within the dataset, and generating selected images of the heart based on the markers in the dataset. The imaging system also includes a memory for storing the images, and a display for displaying the images. The imaging system, and more specifically the image capture device 510, further includes a port communicatively coupled to a network, such as an intra-hospital or intra-clinic network. The port can also be to a telephone network, a wide area network, the internet, or the like. The port can also be to a network that includes web based storage or computing.

Figure 6:
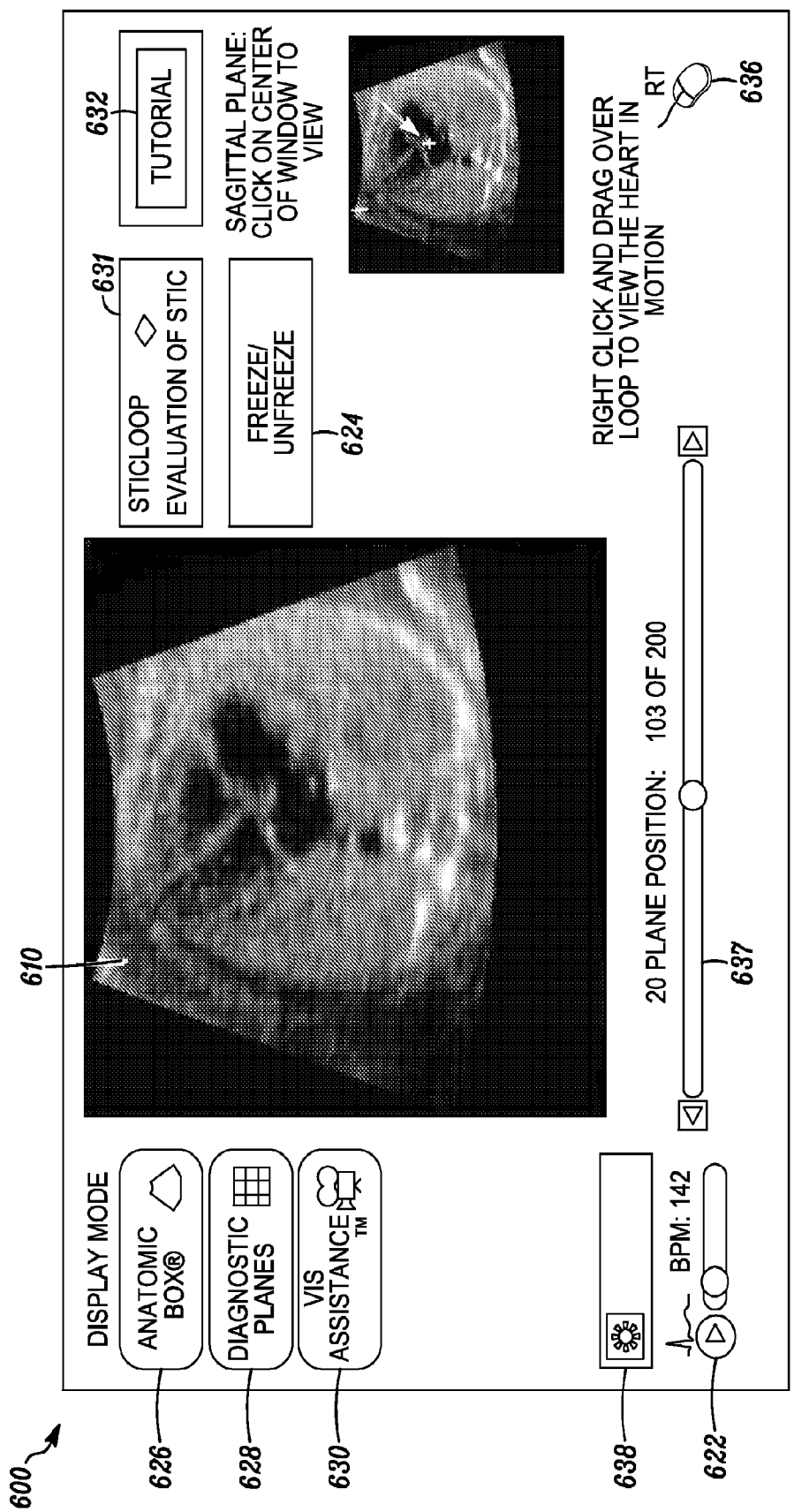
FIG. 6 is an image of a fetal heart as captured by the imaging system, according to an example embodiment.

FIG. 6 is screen shot 600 that includes an image of a fetal heart 610 as captured by the imaging system 500 or imaging capture device 510, according to an example embodiment. The screen shot 600 is part of an interface between the imaging system and a user. The screen shot 600 is a snapshot in time of the interface. The captured image is part of a cine loop with the fetal heart in motion. For screenshot 600, the image has been frozen by the system. The screenshot 600 of the interface includes a button 622 for putting the heart into motion. The area near the button also includes a slider button X which can change the cardiac phase. The button 622 can be clicked upon to put the heart into motion or not in motion when in a particular portion of the phase of the cardiac cycle. The interface also includes a freeze and unfreeze button 624 which causes the STICLoop (two-dimensional cine loop) to scroll continuously through frames or freezes the cine loop so a single image is shown. The interface also includes several display modes, which include an anatomic box 626, a button for diagnostic planes 628 and a button for a VIS-Assistance 630, which is deactivated in this particular interface. There is also a button labeled STICLoop 631. There are other buttons on the interface or screenshot 600 for a tutorial 632, and other instructions displayed in 636. There also buttons for controlling the display including a button 638 for adjusting image color, brightness, midtones, and contrast. Slider button 637 is used to scroll through each frame of the two-dimensional cine loop. When the button 638 is enabled, a dropdown menu shows brightness, midtones, contrast and the like. A menu item is selected and adjusted with the slider buttons.

In another embodiment, a volume loaded into the system includes a heart image in motion, and a two-dimensional cineloop (STICLoop) is scrolling continuously through all the frames. In this embodiment, the criteria for STICloop are listed on the screen. The screen includes a freeze/unfreeze button. When the freeze button is enabled FIG. 6 appears. There is a slider button to allow adjustment of the beats per minute.

Figure 7:
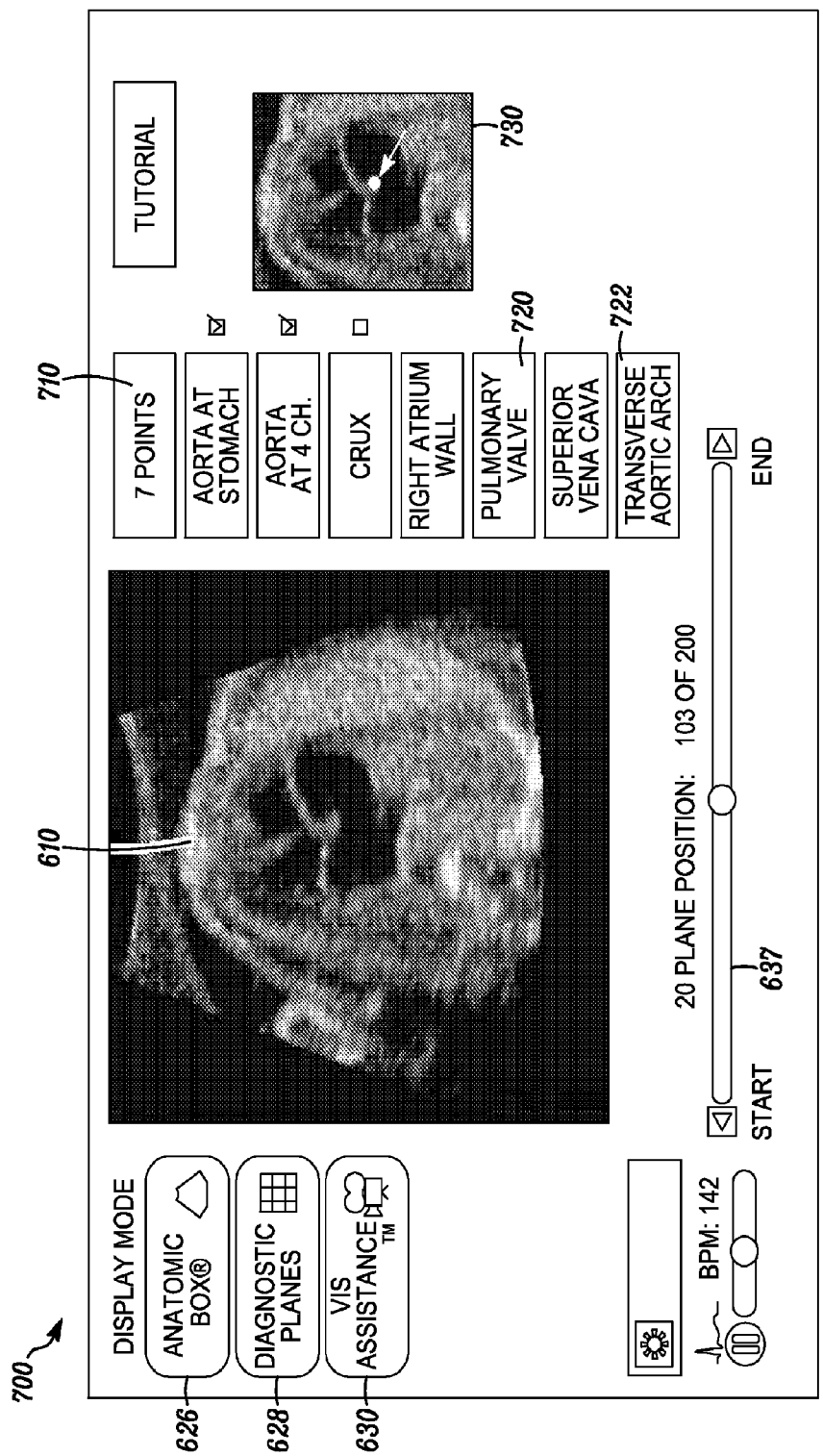
FIG. 7 is an image of an interface presented to a user for marking anatomical portions of the fetal heart, according to an example embodiment.

FIG. 7 is a screenshot 700 an image of an interface, referred to as an Anatomic Box, presented to a user for marking anatomical portions of the fetal heart, according to an example embodiment. The screenshot includes an image from the STIC data set as originally captured by the imaging device 510. On the right-hand side of the image 700 there is included a title 710 indicating that there are seven points to mark in the anatomy of the heart. In this particular instance the number seven is thought to be parsimonious. In other words, the seven markers indicated can be used to generate the necessary diagnostic planes that are desired. The markers are set forth below the title 710. One of the markers 720 is for the pulmonary valve while another of the markers is for the transverse aortic arch 722. The user clicks on the image as instructed by the marker buttons. In response, the interface produces a sample image 730 showing the portion of the anatomy to be marked next. The technician thus merely has to click on the portion of the image 610 which corresponds to the sample image 730. In one embodiment, once a mark has been made the information is saved and an open box is presented next to the button for the anatomical part to be next marked. As shown in FIG. 7, there is an open box positioned adjacent the button for the crux of the heart. The sample image 730 shows the crux marked in the sample. The user marks the crux on the image 610, the box next to the crux button is checked and a box then opens for the next anatomical marker required, which in this case will be the right atrium wall. Being able to control cardiac motion button 622 and adjust cardiac phase (button X) is an important feature in marking of anatomical structures. For example, the phase can be adjusted so the pulmonary valve appears closed. This is done by using slider button X.

The system 500 scrolls through the STIC volume to display the individual slices (one pixel in thickness) as a two-dimensional cine loop (STICLoop). Anatomic Box is used to identify the anatomical structures that would allow geometric modeling of the organ of interest, namely the fetal heart. The marked structures within the volume data set are sufficient to generate spatial coordinates that would provide reliable and accurate reconstruction of the organ. The anatomic box view 700 is used to accomplish the marking of the heart or organ of interest. The system displays a menu identifying the anatomical structures to be marked and does so in a specific order. Information from the crucial marks needed for geometrical modeling through intelligent navigation are obtained by prompting the user to select and mark the anatomical structures needed. In one embodiment the process is simplified since the system 500 scrolls through the volume to a level of the most likely location of the anatomical structure to be marked. The user may need to perform scrolling adjustments to mark anatomical structures appropriately. Once marking of the structure is completed, the system rotates, aligns, dissects and scales the volume data set to display the nine diagnostic planes simultaneously. In one embodiment, the system rotates, aligns, dissects and scales the volume automatically and immediately. In another embodiment, the system rotates, aligns, dissects and scales the volume within several seconds.

Figure 1B:
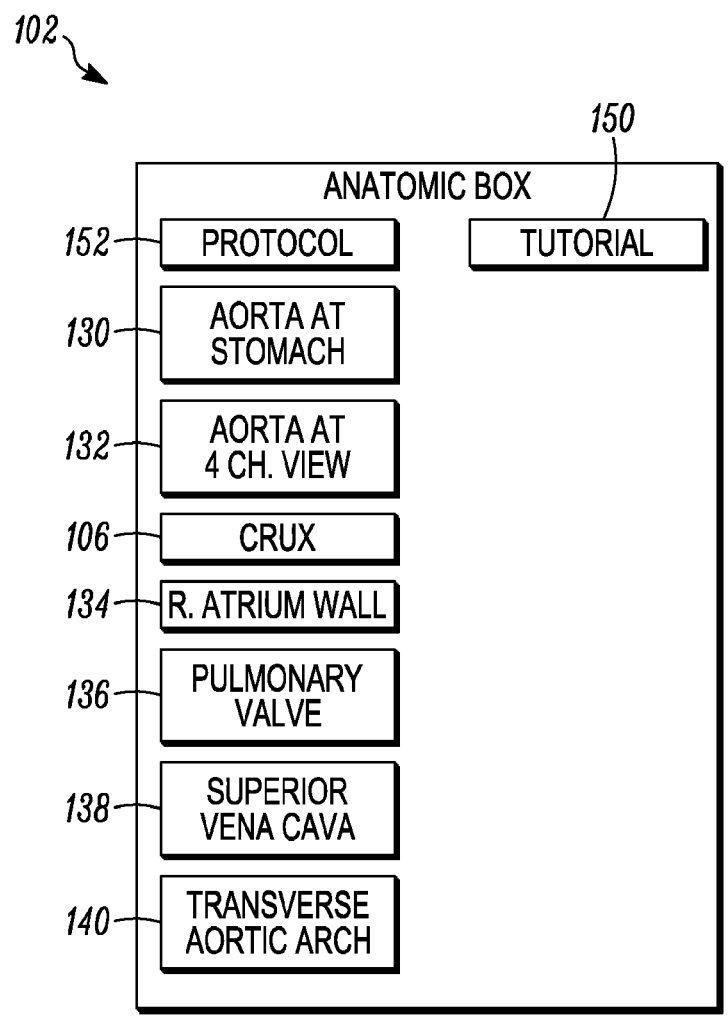
FIG. 1B is a portion of the display shown in FIG. 1A, according to an example embodiment.

FIG. 1A shows an example only of the interface in an anatomic box view, with a collection of sample images showing the fetal anatomy to be marked. In the anatomic box view 100, each of the sample marked views are displayed. Note that each of the sample views includes the mark made and each view has a pointer to the particular anatomical mark as made. The views includes the aorta at the stomach level 110, the aorta at the level of the four chamber view 112, the crux also at the level of the four chamber view 610, the right atrial wall at the level of the four chamber view 114, the pulmonary valve 116, the superior vena cava 118 and the transverse aortic arch 120. FIG. 1B shows a portion 102 of FIG. 1A that appears in the middle of view 100. The portion 102 includes a protocol button 152. In some embodiments, the protocol button has been replaced by a "7 points marking of anatomy" button 710 (shown in FIG. 7) and a tutorial button 150. The tutorial button can be pressed in order to get further instructions on the use of the anatomic box view 100. The portion 102 also includes a button 130 for the aorta at the stomach level, a button 132 for the aorta at the level of the four chamber view, a button 106 for the crux also at the level of the four chamber view, a button 134 for the right atrial wall at the level of the four chamber view, the button 136 for the pulmonary valve, a button 138 for the superior vena cava, and a button 140 for the transverse aortic arch.

There may be instances where the captured image is orientated in a different position or where the anatomical marker may not be in the expected position within the volume. For example, the spine may be located at 3-o'clock. In either instance, during the marking of various anatomical points in the heart, the imaging device or processor 520 within the imaging device 510 recognizes this and produces a pop-up screen. The pop-up screens are either labeled as intelligent alerts or marking alerts. For some alerts, a movie is activated and will automatically play.

Figure 8:
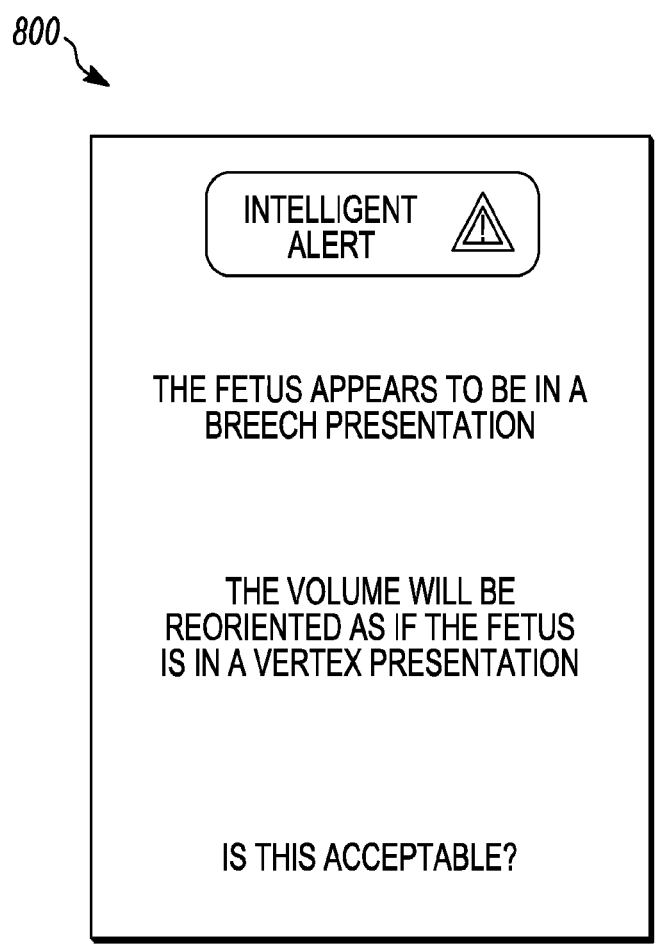
FIG. 8 is an image of an intelligent alert that indicates the baby is in breech presentation, according to an example embodiment.

FIG. 8 is an image of an intelligent alert 800 that indicates the baby is in breech presentation, according to an example embodiment. When a baby is in breech presentation, the cardiac apex points to the right side of the screen. Normally the cardiac apex points to the left side of the screen. The breech presentation can be noted after one anatomical marker is designated. When this condition is detected an intelligent alert 800 is produced. The nature of the intelligent alert is to inform the user that the fetus appears to be in breech presentation and that the volume will be reoriented to the fetal vertex presentation. A prompt is also placed on the intelligent alert 800 to ask if the reorientation to the fetal vertex presentation is acceptable.

Figure 10A:
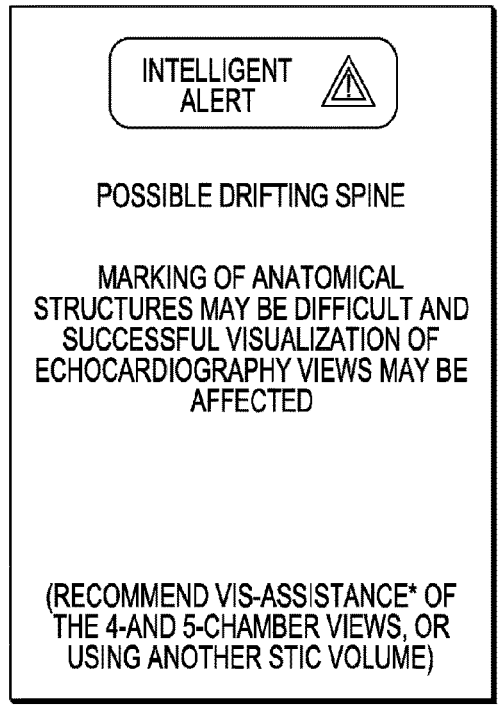
FIG. 10A is an image of an intelligent alert that indicates possible drifting spine, according to an example embodiment.
Figure 10B:
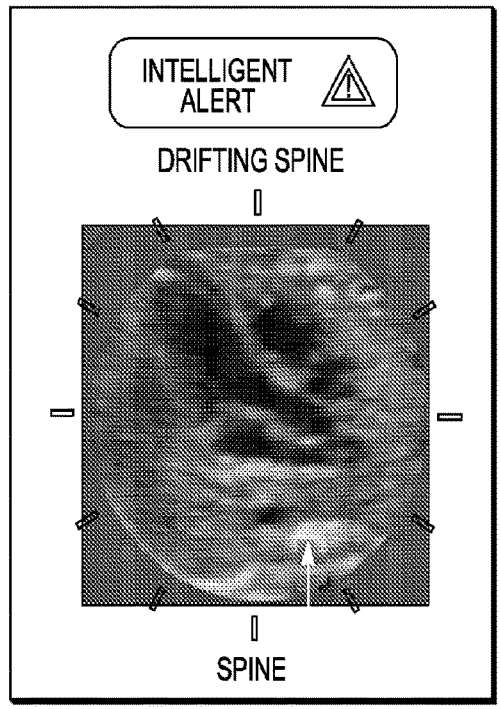
FIG. 10B is an image of a possible drifting spine, according to an example embodiment.

FIG. 10A is an image of an intelligent alert 1000 that indicates a possible drifting spine, according to an example embodiment. FIG. 10B is a movie showing an example of a drifting spine, according to an example embodiment. Now referring to both FIGS. 10A and 10B, intelligent alert for the possible drifting spine 1000 will be further detailed. A drifting spine is when the spine location appears to migrate on the screen. In other words, sequential axial plane should be parallel to one another, similar to the cuts on a loaf of bread. An indirect way of confirming that the planes are parallel is by observing no drifting spine or by reviewing the sequential axial planes and noting the spine position is substantially the same on each of the sequential planes. The drifting spine can be detected after the cross section of the descending aorta at the level of the stomach and at the level of the four chamber view have been marked. If the spine migrates to different positions on the various axial planes an intelligent alert 1000 is produced. It recommends using another STIC volume or taking other corrective action. It also notes that with the drifting spine marking of anatomical structures may be difficult and successful visualization of the echocardiography views may be affected. FIG. 10B shows an example of a drifting spine on actual movie 1020.

Figure 11A:
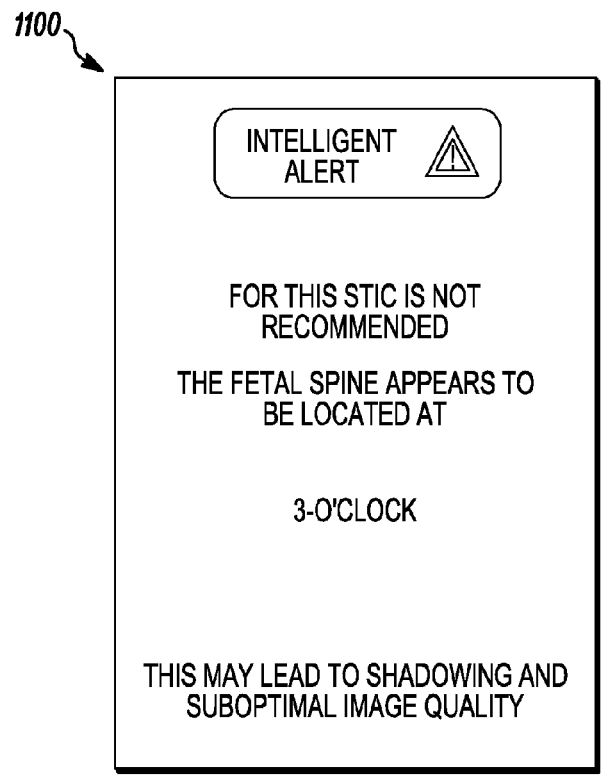
FIG. 11A is an image of an intelligent alert regarding spine location, according to an example embodiment.
Figure 11B:
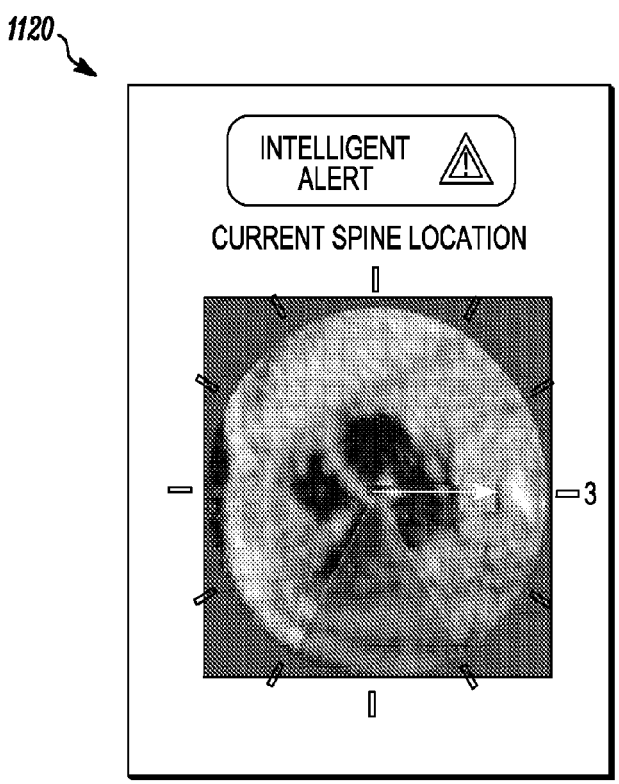
FIG. 11B is an image of a possible location of an anatomical point, according to an example embodiment.

FIG. 11A is an image of an intelligent alert 1100 indicating that the spine is located in a non-recommended position, according to an example embodiment. Generally, it is recommended that the spine be located between five and seven o'clock. FIG. 11B is a movie of an intelligent alert 1120 showing the current spinal location, according to an example embodiment. Now referring both to FIGS. 11A and 11B, the alerts 1100 and 1120 will now be further discussed. The recommended position of the spine is between five and seven o'clock within the volume captured by the image capturing device 510. When the spine is outside of the recommended range, an alert is produced such as alert 1100, and this may lead to shadowing in the captured volume and suboptimal image quality. The intelligent alert 1100 indicates that the particular volume or STIC is not recommended for use. The alert 1100 appears after three anatomical structures have been marked using the anatomical box view 700 (shown in FIG. 7). The three markers include the aorta at the stomach level, the aorta at the four chamber view level, and the crux at the four chamber view level.

Figure 12A:
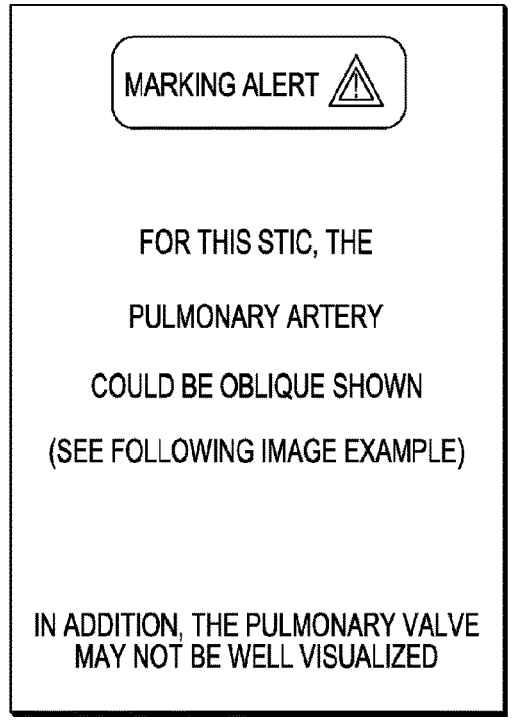
FIG. 12A is an image of a pulmonary artery marking alert, according to an example embodiment.
Figure 12B:
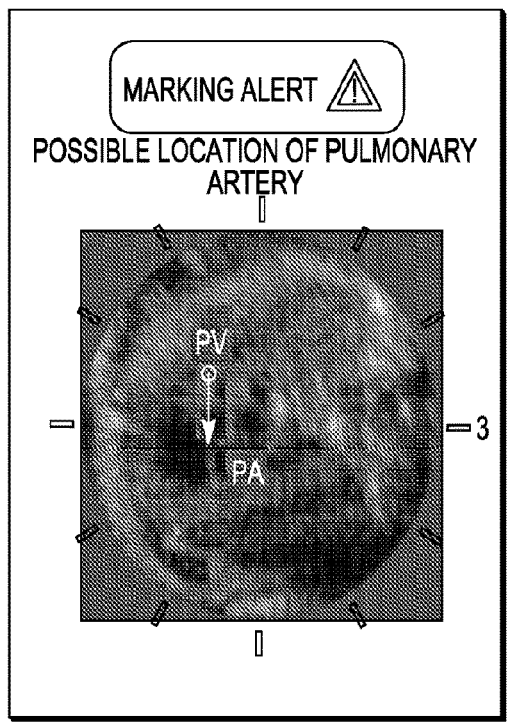
FIG. 12B is an image of a possible location of an anatomical point, according to an example embodiment.

FIG. 12A is an image of a marking alert 1200 for the pulmonary artery, according to an example embodiment. FIG. 12B is an image 1220 of a possible location of an anatomical point, according to an example embodiment. The marking alert 1200 notifies the user that the pulmonary artery could be oblique. It also notifies the user that the pulmonary valve may not be well visualized. There may be difficulty in marking the pulmonary valve. Once the right atrial wall is marked, the marking alert in the movie will appear on the screen or interface for the user. The image 1220 is actually a movie showing the pulmonary valve and its possible location.

Figure 13A:
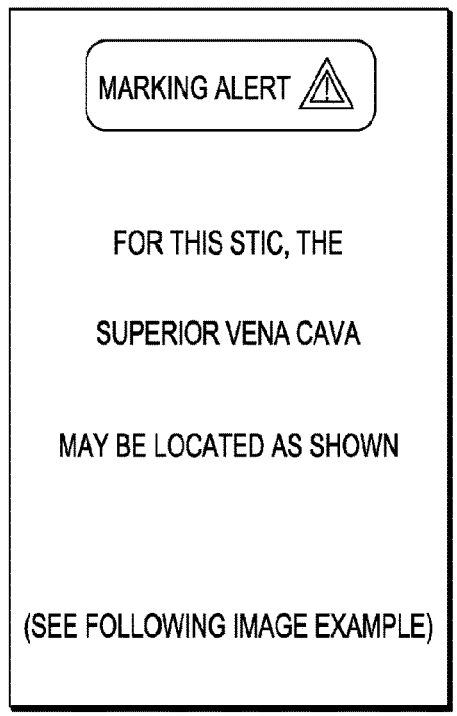
FIG. 13A is an image of a superior vena cava marking alert, according to an example embodiment.
Figure 13B:
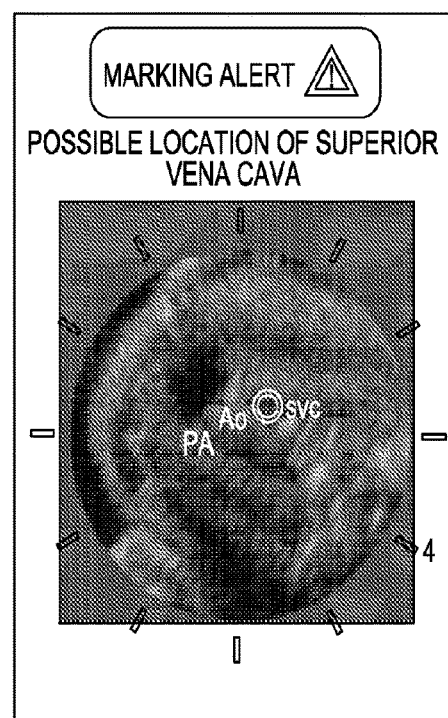
FIG. 13B is an image of a possible location of an anatomical point, according to an example embodiment.

FIG. 13A is an image 1300 of a marking alert indicating that the superior vena cava is in an unexpected position or location, according to an example embodiment. This alert normally occurs after the pulmonary valve alert has been displayed and the pulmonary valve has been marked. FIG. 13B is an image 1320 of a possible location of an anatomical point, according to an example embodiment. The image 1320 is a movie that shows the possible location of the superior vena cava.

Figure 9A:
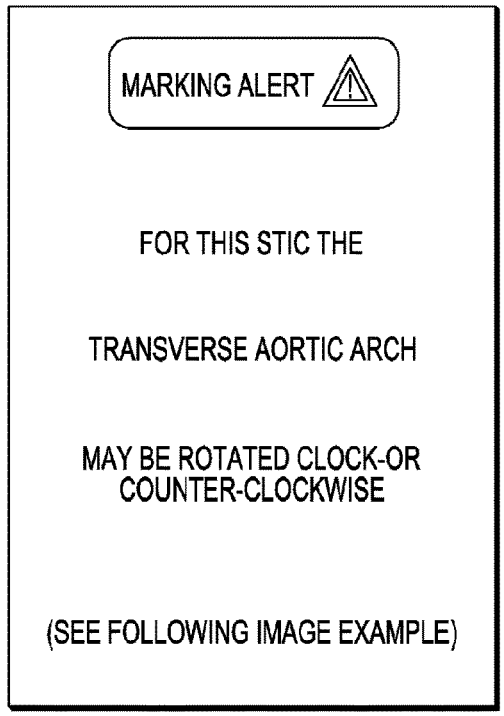
FIG. 9A is an image of a transverse aortic arch marking alert, according to an example embodiment.
Figure 9B:
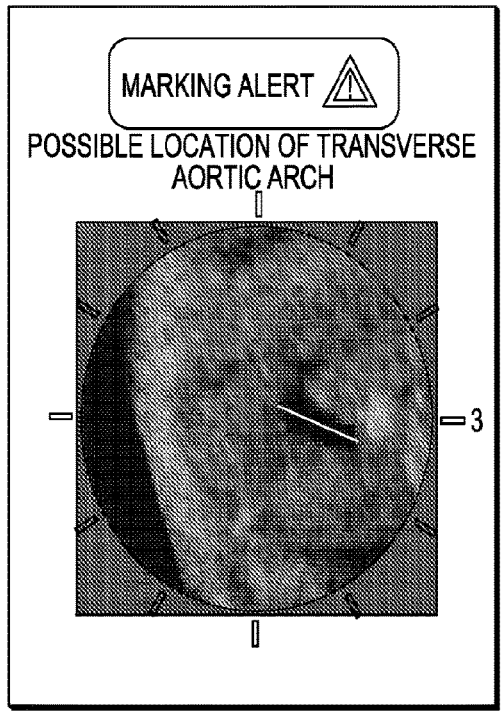
FIG. 9B is an image of a possible location of an anatomical point, according to an example embodiment.

FIG. 9A is an image of a marking alert 900 for the transverse aortic arch, according to an example embodiment. FIG. 9B is a movie 920 of a possible location of the transverse aortic arch, according to an example embodiment. Now referring to both FIGS. 9A and 9B, these alerts will be further detailed. The alert 900 notifies the user that the transverse aortic arch may be rotated either clockwise or counterclockwise. As a result of this rotation, it may be difficult to mark the transverse aortic arch. The movie 920 shows the possible location of the transverse aortic arch in the STIC volume.

Once marking of the seven anatomical structures has been completed within the STIC volume of the fetal heart, geometric modeling of the fetal heart occurs and the system 500 generates a number of diagnostic views of the heart in several seconds. In the case of a fetal heart STIC volume, the views will be nine fetal echocardiography views (diagnostic planes). The system navigates, finds, and extracts and displays the diagnostic planes without operator intervention. More specifically the system rotates, aligns, dissects, and scales the volume data set to display nine cardiac diagnostic planes simultaneously.

Figure 14:
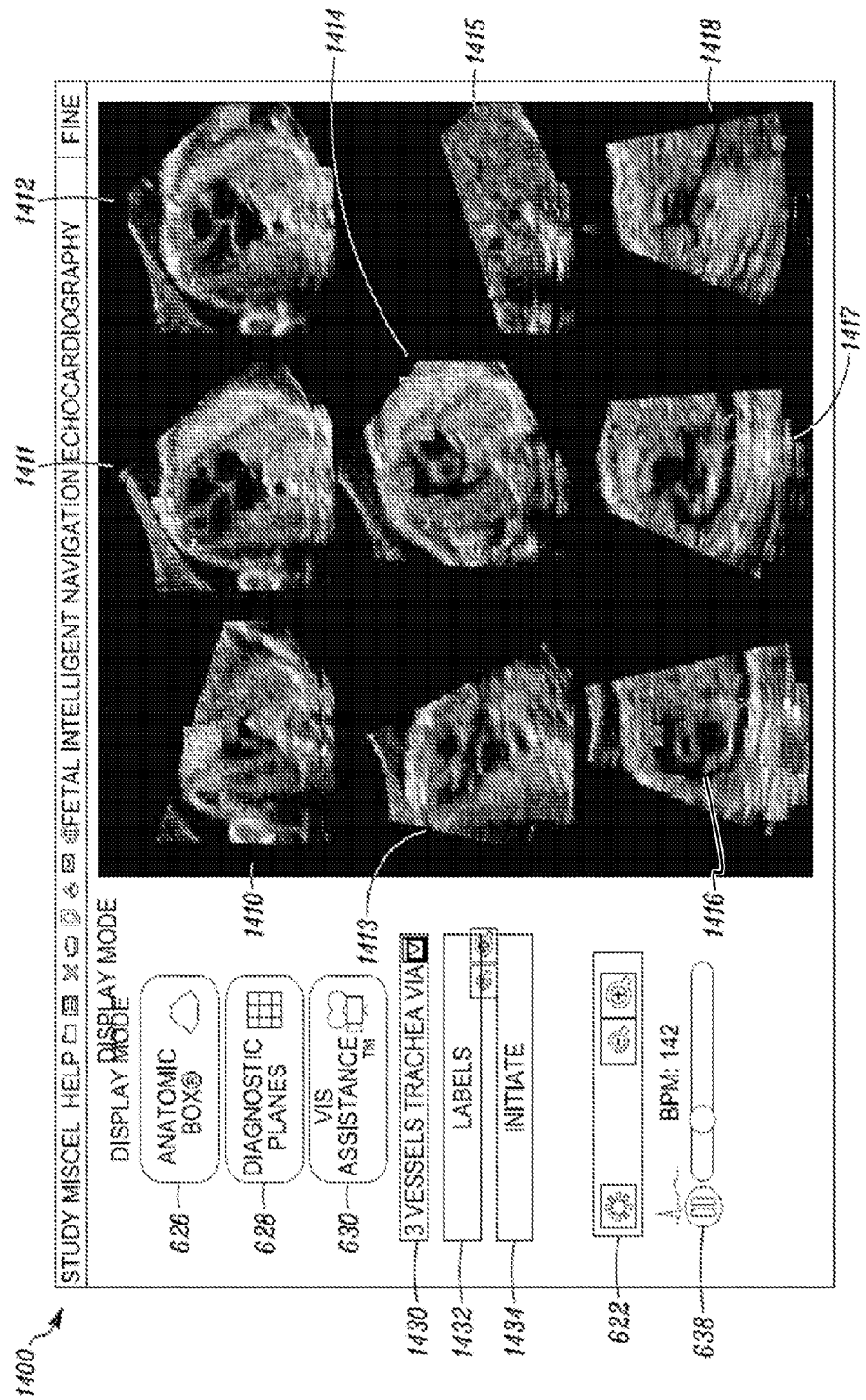
FIG. 14 is an image of an interface presented to a user to showing a plurality of diagnostic planes, according to an example embodiment.

FIG. 14 is an image of an interface 1400 presented to a user showing a plurality of diagnostic planes, according to an example embodiment. The image of the interface 1400 is in the form of a screenshot which is a snapshot of the interface at a particular time. As shown in FIG. 14, the nine diagnostic views are displayed simultaneously. The nine diagnostic views include a three vessels and tracheal plane 1410, a four chamber plane 1411, a five chamber plane 1412, a left ventricular outflow tract plane 1413, a short axis view of great vessels and right ventricular outflow tract plane 1414, and abdomen/stomach plane 1415, a ductal arch plane 1416, and aortic arch plane 1417, and a superior and inferior vena cava plane 1418. The view also includes the various viewing modes, namely the anatomic box view 626, the diagnostic planes view 628, and the VIS-Assistance view 630. The view also includes the control 622 for adjusting image color, brightness, midtones, and contrast as well as a slide bar and a pause and play control 638 for putting the heart into motion/no motion, changing the cardiac phase, and changing beats per minute The display also includes an indication of the beats per minute (BPM). As shown in this view the VIS-Assistance® view 630 also includes a drop-down menu 1430 that includes all of the various fetal echocardiography views. As shown the drop-down menu 1430 is currently referencing the view 1410 that corresponds to three vessels and the trachea view. The image or screenshot 1400 also includes a labeling button 1432 and an initialization button 1434. The labeling button 1432 allows the user to press the button so that each of the views is labeled and the anatomical structure(s) within each of these views is also labeled automatically. For example, in the image or screenshot 1400 the four chamber view 1411 includes the left ventricle, the right ventricle, the left atrium and the right atrium. The automatic labeling of the anatomical structures within the diagnostic planes as possible because the system 500 infers the actual location of the structures in space. This occurs regardless of the way in which the volume data set was acquired. The purpose of such labeling is to assist the recognition of the anatomical structures, and to allow images generated for a particular case to be compared with what is considered normal. Similar labeling of the nine fetal echocardiography views (i. e.

diagnostic planes), left and right sides of the fetus, and the cranial and caudal ends is also possible. The labeling is distinctive because stays with the corresponding anatomical structures even as the images increase in size or zoomed or reduced in size. FIG. 14 and other screen shots, include a negative and a positive magnifying glass buttons for controlling an amount of zoom down and zoom up, respectively. It should be noted that the labeling is carried with the images when they are increased or decreased in size using the zoom buttons. The labeling is an optional feature. Pressing the labeling button activates this features at all areas of labeling.

Figure 15:
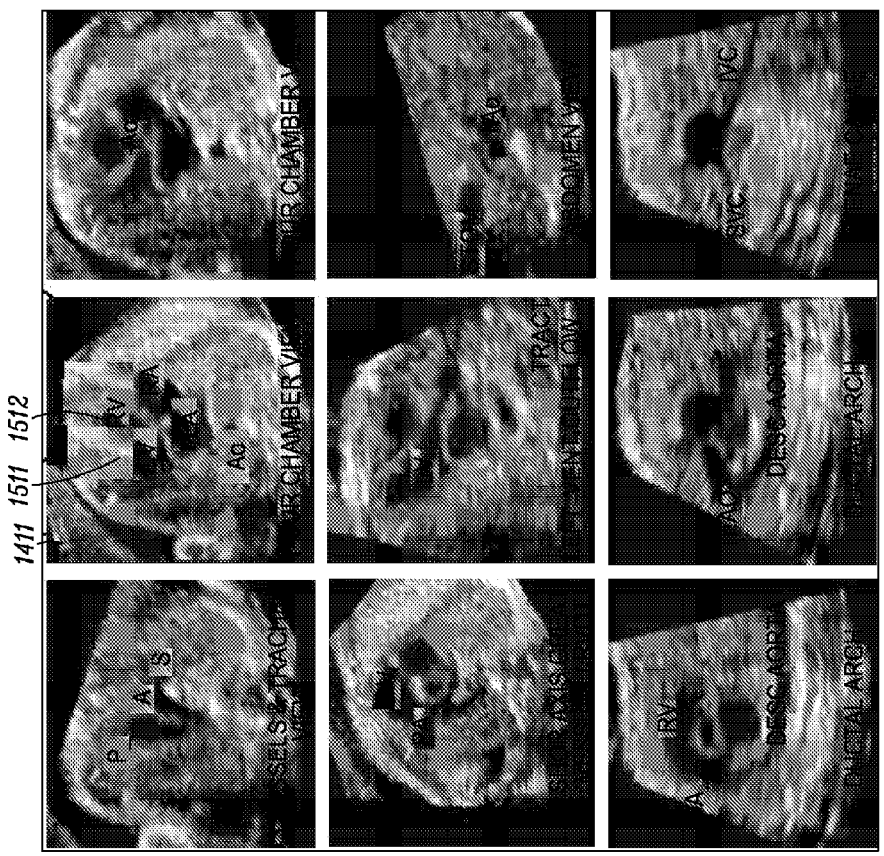
FIG. 15 is an image showing the labeling of the plurality of diagnostic planes, according to an example embodiment.

FIG. 15 is an enlarged image 1500 showing a portion of the screenshot or image 1400 and specifically showing the labeling of the plurality of diagnostic planes, according to an example embodiment. Again looking at the four chamber view 1411 includes the left ventricle 1511, the right ventricle 1512, the left atrium and the right atrium are labeled.

Figure 19:
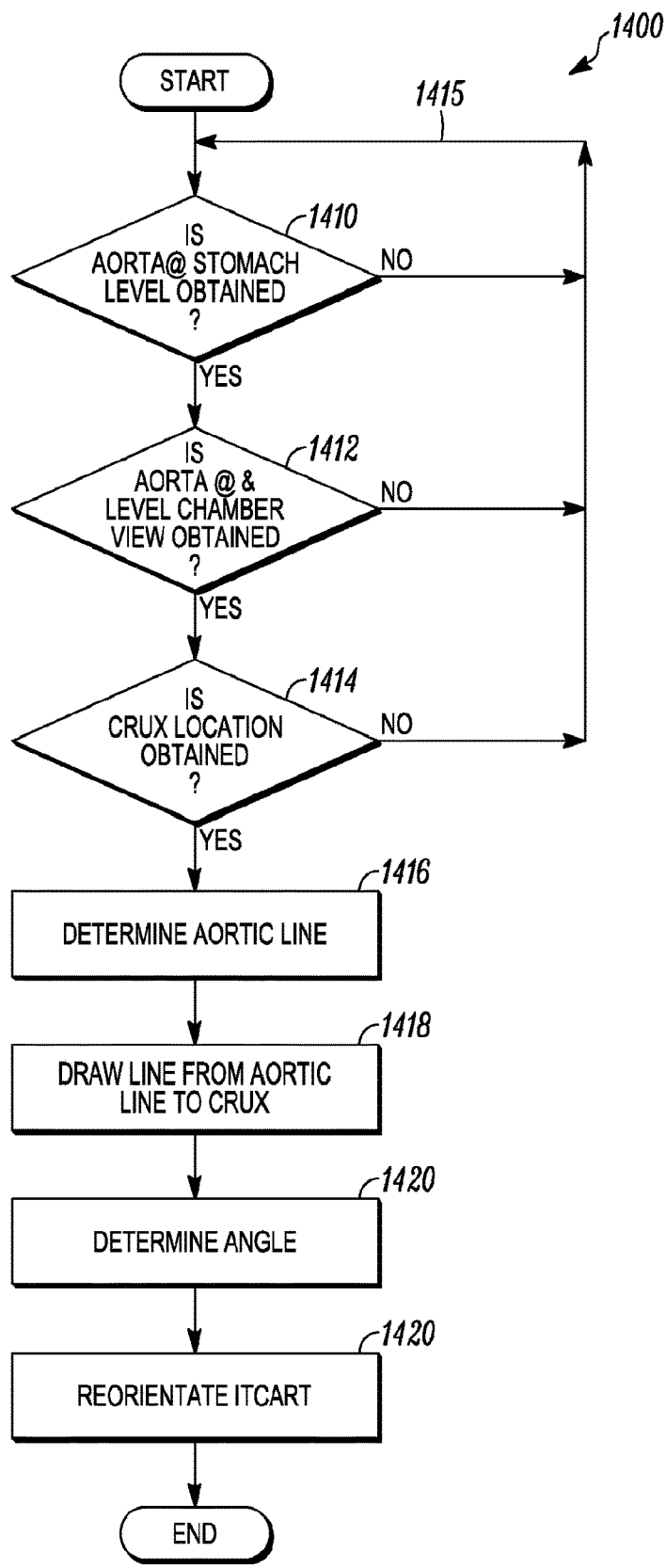
FIG. 19 is representation of a decision tree which is used to generate a diagnostic plane location from one or more marked anatomical points, according to an example embodiment.

Obtaining the various diagnostic views and orientating and scaling the heart from the obtained STIC volume can be done in any number of ways. In one embodiment, the method used is by applying the data to a decision tree. FIG. 19 is flow diagram 1400 representation of a decision tree which is used to determine the orientation and rotational location from one or more marked anatomical points, according to an example embodiment. The flow diagram 1400 includes a decision as to whether the aorta mark at the stomach level has been obtained 1410. If yes the next decision is made with respect to whether the aorta mark at the four chamber view level has been obtained 1412. If yes, the next step is determined if the crux anatomical mark location has been obtained 1414. If the answer to any of these decisions is no then there is a return to the beginning of obtaining the anatomical marks, as picked up by arrow 1415. From the two aorta marks obtained, the aortic line can be determined 1416. The aortic line is the line from the top to the bottom of the heart or vice versa. From some of this information, the orientation of the fetus being in the breech position can also be determined. When the fetus is in the breech position the cranial end will be at a position where the caudal end is normally found. The information from the location of the crux can be used to draw line from the crux position or location to the aortic line 1418. An angle within the obtained volume can be determined 1420. Depending upon the angle, the volume can be reoriented to reorient the heart as depicted by 1422.

With respect to the diagnostic planes or fetal echocardiography views that are generated, decision trees can be used to determine the location of these various diagnostic planes.

Of course there are anatomical variations in fetal organs, such as the heart. As a result, in some instances, one or more of the diagnostic planes may not be placed so as to convey the information required by the user, such as a sonologist. In such an instance, sinologist the VIS (virtual intelligent sonographer) assistance view and function can be used.

FIG. 17 is an image 1600 showing the drop down menu 1610 for selecting the echocardiographic view to which VIS-Assistance is to be applied, according to an example embodiment. Once the particular diagnostic plane or echocardiographic view has been selected, the VIS-Assistance function 1630 is selected and applied to the diagnostic plane, as shown in FIG. 16, which shows an image of the prompt for selecting VIS-Assistance, according to an example embodiment. The VIS assistance function is essentially a look or view in the neighborhood of the plane as selected. The image can be automatically manipulated to see if an additional and better viewing can be obtained through a slight variation of the plane. In one embodiment, various video clips for various views are determined and shown when the VIS assistance function is selected. For example, parallel planes may be shown and the plane may be tilted or the like. In one embodiment, even the sequence is determined as part of the VIS assistance function.

Figure 18:
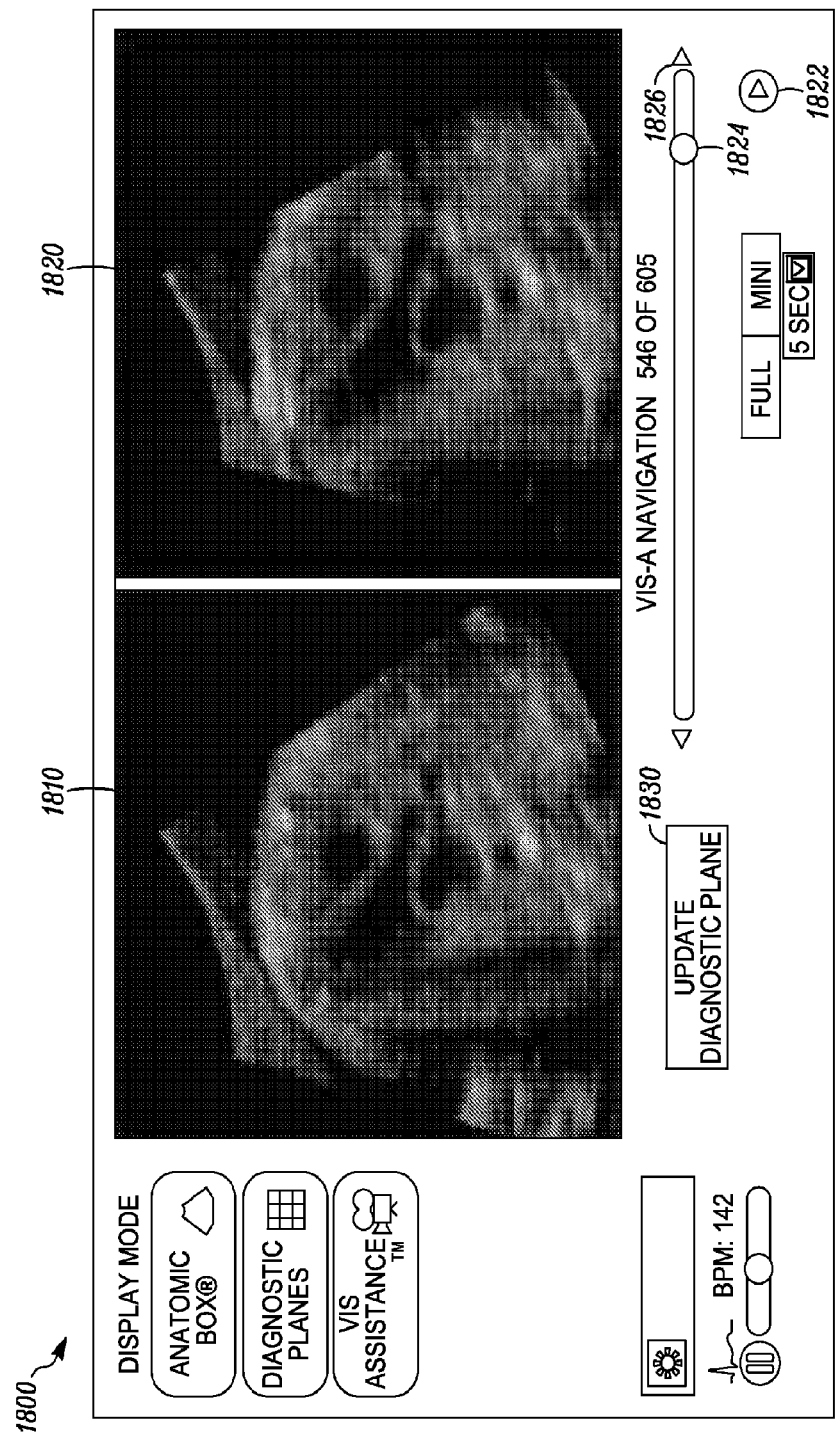
FIG. 18 is an image showing a generated diagnostic plane and a generated diagnostic plane that has been modified using the VIS-Assistance, according to an example embodiment.

FIG. 18 is an image or screenshot 1800 showing a generated diagnostic plane 1810 and a generated diagnostic plane that as it is being modified 1820 using the VIS-Assistance, according to an example embodiment. The modified diagnostic plane 1820 includes moving the plane through various orientations. The viewer is able to stop the video of the modified diagnostic plane 1820 using the pause or play which 1822. The viewer can also move the target 1824 on the slider bar 1826 to move to a different frame in the video. If the user sees a plane that is improved over to the plane 1810, the user has the opportunity to update the diagnostic plane using the update switch 1830. The video clip associated with the modified diagnostic plane 1820 includes several characteristics. One embodiment, the navigational movements in the volume as picked up by the video clip are, without operator intervention. In other words, it can be said that is automatic and operator independent. The navigational movements are also consistent through the volume each time the video clip is activated. Should also be noted that the navigational movements are unique and fluid. For example, through the VIS assistance function, swinging in oblique planes can occur from a single pivot point in a sequential series of movements equal distance from each other. This precision and consistency cannot be achieved through live two-dimensional sonography or manual navigation of a volume data set. Still another characteristic is that the video clips typically have a shorter time duration (less than four minutes) than that of manual navigation. The video clips can show the appropriate azimuth. This is important because tilted planes may cause sub optimal visualization of anatomy or may raise the suspicion of an abnormality in the heart that is really non-existent. Another example that illustrates the application of this function to the fetal heart relates to the left ventricular outflow tract diagnostic plane. The left ventricular outflow tract diagnostic plane may not show excursion of the mitral or aortic valve leaflets optimally. By activating VIS assistance various navigational movements will occur around the area of these valves so as to show them.

An imaging method includes obtaining a dataset volume of a heart using spatio-temporal image correlation in an ultrasound imaging mode, marking a plurality of anatomical points of the heart within the obtained dataset, and generating a plurality of diagnostic images of the heart from the marked anatomical points of the heart in the obtained dataset. Marking the plurality of the anatomical points of the heart includes marking at least a plurality of the following anatomical points of the heart: an aorta point in a cross-section of the aorta at level of stomach; an aorta point in cross-section of the aorta at level of the four chamber view of the heart; a crux point in a view of the cross-section of the aorta at level of the four chamber view of the heart; a line through the ventricular septum, the crux point, and terminating at the right atrial wall of the heart; a pulmonary valve point substantially in the middle of the pulmonary valve of the heart; a superior vena cava point substantially in the middle of the superior vena cava of the heart; and a transverse aortic arch point. In one embodiment, the imaging method also includes marking at least one line corresponding to anatomical portions of the heart. In another embodiment, all of the marks are made on the image of the captured data of the heart. Marking the plurality of the anatomical points of the heart, in some embodiments, includes presenting a sample view of a sample heart with a marked anatomical portion, presenting a similar view of the heart from the obtained data set, and prompting a response for marking the heart from the obtained data set. In one embodiment, marking the plurality of the anatomical points of the heart further comprises labeling an anatomical point in response to receiving a response for marking the heart. The label or labels are displayed on a computer monitor. A plurality of the anatomical points of the heart can be marked in the same or a similar way and also labeled and displayed after placing the mark on the obtained data set. In one embodiment, a plurality of sample views of a sample heart marked at an anatomical portion are presented. A plurality of unmarked views of the heart from the obtained data set that correspond to the plurality of sample views are also presented. A response for marking the plurality of unmarked views of the heart from the obtained data set is prompted, and a plurality of diagnostic images from a plurality of marks received as responses are generated. In one embodiment of the imaging method a marked view of the heart from the obtained data set is reoriented upon detecting a fetal heart from a baby in a breech presentation. A warning note is displayed, in some embodiments, indicating that the baby is in a breech presentation. The warning note includes a prompt seeking a response that the reorientation action is acceptable. In still another embodiment, the imaging method includes adjusting at least one of the generated diagnostic views by changing the angle of at least one of the generated diagnostic views. In one embodiment, the generated diagnostic views are in planes. Adjusting includes a set of steps for changing the view slightly to get a better view of the area of interest. In one embodiment, a computer is able to conduct an adjustment. A computer generally makes these adjustments as a set of predetermined steps. In some embodiments, adjusting at least one of the generated diagnostic views shifts the diagnostic view to a parallel plane within the dataset volume and in another embodiment, the angle of the view may be changed. In still another embodiment, both of these actions can be taken to effectuate the adjustment. Generating a plurality of diagnostic images of the heart from the marked anatomical points of the heart from the obtained dataset includes using information from at least two of the marked anatomical points in a decision tree to determine the plane of diagnostic image. The information is placed in a decision tree. A series of "yes" or "no" type questions are answered. The outcome is used to generate the diagnostic view. The generated plurality of diagnostic images are displayed on a computer display. The plurality of diagnostic images generated from the obtained dataset includes at least a plurality of the following fetal echocardiography views: a four-chamber view; a five-chamber view; a left ventricular outflow tract view; a short axis view of great vessels/right ventricular outflow tract view; a three-vessels and trachea view; an abdomen/stomach view; a ductal arch view; an aortic arch view; and a superior and inferior vena cava view. The above method can be implemented as a computer method on a machine that operates on an instruction set and is converted to a specialized machine as a result.

Intelligent Navigation

"Intelligent navigation" refers to the examination of a volume dataset whereby identification of key anatomical landmarks (Anatomic Box®, Medge Platforms Inc., New York, N.Y.) allows a software system (SONOCUBIC®, Medge Platforms Inc., New York, N.Y.) to: 1) generate a mathematical reconstruction of the organ of interest; and 2) navigate, find, extract, and display specific diagnostic planes using an algorithm that is both predictable and adaptive. In one embodiment, this is done automatically and instantaneously. Intelligent navigation includes two main features: 1) Anatomic Box®; and 2) Virtual Intelligent Sonographer Assistance (VIS-Assistance®).

After a STIC volume dataset has been acquired and saved, the operator uses Anatomic Box® to identify and mark key anatomical structures in a pre-determined sequence on the two-dimensional sweep (original transducer acquisition leading to the volume dataset) to "trigger" intelligent navigation. The key elements that allow mathematical reconstruction of the organ of interest and its relationships are the spatial coordinates generated by the anatomical landmarks selected. This is possible because the landmarks in different planes of the heart allow inferences of the anatomical relationships in multiple dimensions. Once the marking is complete, the system substantially automatically and substantially instantaneously rotates, aligns, dissects, and scales volume dataset to display information of the volume dataset to depict the diagnostic planes of interest, which can be displayed simultaneously in the same template. Of course, the time for transforming the marked anatomical points to diagnostic planes is dependent on the processing power of an imaging device 510. In one embodiment, the generation of the diagnostic views is completed in 3 seconds. In other imaging systems, the necessary operations for generating the diagnostic views may take a longer time or even a shorter time. Regardless, the time needed for generating these views is much less than needed for even a skilled technician to manually produce the diagnostic views. Thus, substantially instantaneously refers to the time necessary. Substantially automatically in this instance refers to the time between accomplishing the final anatomical mark by an operator which triggers the diagnostic views. It is realized that there are many steps that need operator inputs before the triggering event. For STIC volumes, cardiac diagnostic planes are shown as a cine-loop of a complete single cardiac cycle in motion. Each diagnostic plane may also be manually navigated (e.g. rotated on x, y, z, diagonal axes, parallel shift) independently if desired.

Development Phase of Fetal Intelligent Navigation Echocardiography (FINE)

The development of the FINE method was based on STIC volume datasets obtained from patients examined at the Detroit Medical Center/Wayne State University and at the Perinatology Research Branch, NICHD, NIH, DHHS. All patients had been enrolled in research protocols approved by the Institutional Review Board of the NICHD, NIH and by the Human Investigation Committee of Wayne State University.

Figure 3:
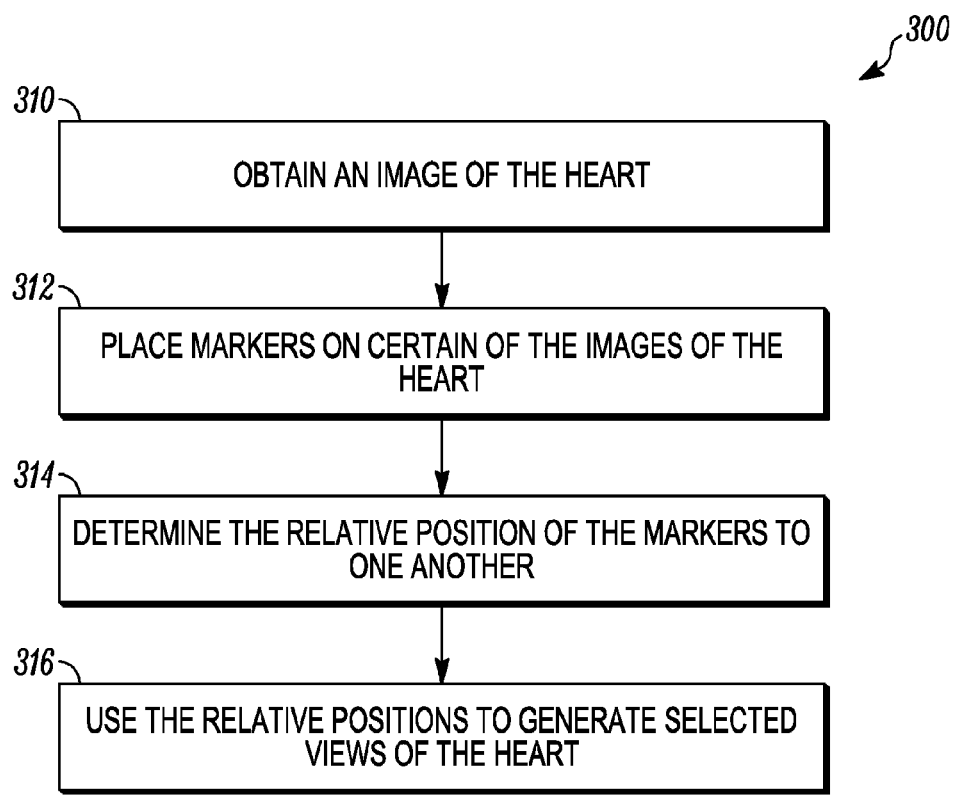
FIG. 3 is a flow diagram associated with a computerized method, according to an example embodiment.

The basic method is set forth in FIG. 3. FIG. 3 is a flow diagram associated with a computerized method 300, according to an example embodiment. The computerized method 300 includes obtaining an image of the heart 310, placing markers on certain of the images of the heart 312 and determining their relative position to one another 314 and using the relative positions as well as set of decision trees to generate selected views of the heart 316. The selected views of the heart can be orientated for analysis when rendered on a display or screen. In other words, the selected views of the heart can be along diagnostic planes for a doctor or other medical professional to use in diagnosing potential problems with the heart.

Using STIC technology (Voluson E8 Expert; GE Medical Systems), 4D volume datasets of the fetal heart were acquired from an apical four-chamber view using hybrid mechanical and curved array transducers (2-5 or 4-8 MHz) by transverse sweeps through the fetal chest in patients examined in our unit. Acquisition times ranged from 7.5 to 12.5 seconds, and the angle of acquisition ranged between 20° and 45°, depending on fetal motion and gestational age. Fifty-one volume datasets of normal hearts (19.5-39.3 weeks of gestation) were selected by the investigators. The criteria for inclusion were: 1) fetal spine was positioned between the 5- and 7-o'clock positions (minimizing the possibility of shadowing from the ribs or spine); and 2) the upper mediastinum and stomach were contained in the volume. Five fetuses (9.8%) were in breech presentation, so that the cardiac apex was originally pointing to the right side of the screen. All STIC datasets were used to develop and refine the FINE method in the initial phase of work.

A commercially available software system that is specifically designed for volumetric analysis and rendering was used to analyze the STIC datasets (SONOCUBIC Classic Blue Series, Medge Platforms Inc., NY, N.Y.). This system includes a suite of tools considered suitable for the evaluation of STIC volumes. For example, the tool called Anatomic Box® can be used for the marking of anatomical structures and subsequent automatic rendering of volume datasets. In addition, the software allows the manipulation of parallel tomographic slices so that they can be tilted independently. This was considered important to display anatomical structures such as the great vessels which may not be imaged appropriately when parallel dissection is used. Also, an "auto-label" feature was used to designate a particular anatomical structure (i.e. right and left ventricles, aorta, etc.) as well as the standard echocardiographic planes (e.g. four-chamber view, left ventricular outflow tract).

Development of the FINE method first involved evaluation of the different anatomical landmarks as to their potential for generating a geometric model of the fetal heart which could be dissected to display echocardiographic views. Structures considered included: apex of the heart, atrioventricular valves, crux, atrial walls, ventricular septum, aorta, pulmonary artery, superior and inferior vena cava, and the like. The minimum number (parsimonious) of anatomical landmarks required to produce a geometric model of the fetal heart from which the fetal echocardiography views can be extracted was determined. Selection of anatomical landmarks took into account the need to reduce operator error. Anatomical landmarks that could easily be identified by sonologists were preferred. For example, structures observed at the level of the four-chamber view of the heart such as the crux were selected because this is the most easily and commonly obtained plane in fetal echocardiography. Additional landmarks were required because it became clear that an adequate modeling of the fetal heart could not be achieved without including landmarks outside the four-chamber view. Repeated iterations were performed to select informative landmarks. Additional potential landmarks were selected based upon their potential to add more information to construct a geometric model. A large number of landmarks were discarded because they failed to provide informative or reliable information.

After the marking of seven anatomical structures within the heart, the Anatomic Box® feature was used to perform the calculations required to reconstruct the heart in three dimensions and generate the conventional fetal echocardiography views that had been prespecified before the onset of the project. Nine views were considered desirable: 1) four-chamber; 2) five-chamber; 3) left ventricular outflow tract; 4) short axis view of great vessels/right ventricular outflow tract; 5) three-vessels and trachea (3VT); 6) abdomen/stomach; 7) ductal arch; 8) aortic arch; and 9) superior and inferior vena cava.

Reorientation of fetal images and diagnostic planes was enabled so that the images would be consistently displayed each time (e.g. breech to "vertex", spine at 6 o'clock) regardless of fetal lie and position. This is important so that marking anatomical structures would be easier. Each of the images would be expected to be in the same location on the display or screen. Therefore, the orientation of the fetal images is standardized for: 1) axial images (fetal left on the left-hand side of the screen, and fetal right on the right-hand side of the screen, and the cardiac apex always points to the upper left corner of the screen); and 2) longitudinal images (cranial position on the left-hand of the screen, and caudal position on the right-hand of the screen). Thus, the fetal head would always point towards the left side of the display or screen.

The nine views are automatically labeled, namely the left and right side of the fetus, cranial end and caudal end direction, as well as the atrial chambers, ventricular chambers, great vessels (aorta and pulmonary artery), superior and inferior vena cava, and stomach. This assists readers of the images in recognizing anatomical structures and enables comparisons of the images generated for a particular case to what is considered a normal view.

Virtual Intelligent Sonographer Assistance (VIS-Assistance™)

The authors recognize that the nine echocardiographic planes represent a recommendation of professional organizations to simplify and standardize among units the examination of the fetal heart. However, the complex anatomy of the fetal heart and anatomical variations may require additional interrogation of a given diagnostic plane. To accomplish this, a tool called the Virtual Intelligent Sonographer Assistance (VIS-Assistance) was developed, which is operator independent. This tool allows spontaneous sonographic navigation and exploration of surrounding structures in each of the nine diagnostic planes (e.g. four chamber view). This is possible since there was a volume dataset acquired (vs. two-dimensional static image). As a result, when VIS-Assistance is activated for each diagnostic plane, the user receives assistance from a "virtual" sonologist that is comparable to a live sonologist performing manual sonography. Both VIS-Assistance and a live sonologist perform ultrasounds which are purposeful and targeted towards visualizing specific structures. Similarly, navigational movements in VIS-Assistance are nonrandom and intelligent due to the design of one or more pivot points which change, and around which sequential movements are centered. VIS-Assistance displays the equivalent of a video clip for further sonographic investigation of any diagnostic plane. The duration of VIS-Assistance for each echocardiographic view ranges from 32 seconds (abdomen/stomach) to 3 minutes 30 seconds (five-chamber view).

VIS-Assistance was developed to achieve the following: 1) automatic navigation through the sonographic volume (decreased operator dependence); 2) consistent navigation through the volume each time VIS-Assistance is activated; 3) unique and fluid navigational movements through the volume, which would be difficult or impossible to perform otherwise with live scanning or manual navigation of a volume dataset; and 4) short (<4 minutes) duration of VIS-Assistance for each diagnostic plane. In some embodiments, VIS-Assistance is also used to tilt planes from a position where the visualization of anatomy is suboptimal to a position where the visualization of anatomy is better than the suboptimal position.

For four specific cardiac VIS-Assistance (3VT, left ventricular outflow tract, short axis view of great vessels/right ventricular outflow tract, abdomen/stomach), it was pre-specified that certain anatomical structures should be visualized (along with the echocardiographic view). The anatomical structures should be visualized by VIS-Assistance include: 1) 3VT view: three-vessel view (3VV), pulmonary valve, and transverse aortic arch view; 2) left ventricular outflow tract view: mitral valve, aortic valve, ventricular septum; 3) right ventricular outflow tract view: pulmonary valve and tricuspid valve; and 4) abdomen/stomach view: stomach and four-chamber view (to determine situs). Moreover, for the four-chamber view VIS-Assistance, the atrial septum and pulmonary veins often could be visualized.

The FINE method includes the display of cardiac diagnostic planes and VIS-Assistance® and was developed after examining STIC volumes multiple times. Each round of testing involved examining 459 diagnostic planes (51 STIC volumes×9), and 459 VIS-Assistance AVI clips (51 STIC volumes×9), for a total of 918 images.

Testing Phase of Fetal Intelligent Navigation Echocardiography (FINE)

After the development phase was completed, the FINE method was tested in a new set of 50 STIC volume datasets selected from patients previously examined and diagnosed to have a normal heart. Volume datasets included in this phase were obtained from fetuses with gestational ages between 18 and 37 weeks. Ten fetuses (20%) were in a breech presentation.

Each STIC volume was first evaluated to determine its appropriateness before the FINE method was applied. STICLoop™ was developed to facilitate detection within the 2D cineloop of: 1) discontinuity or undulating movements that could modify anatomical structure representation due to motion artifacts or errors in STIC assembly; 2) azimuth issues (tilted acquisitions); and 3) "drifting spines" in which the spine location migrates on the screen. Once the STIC volume was loaded into the software system (SONOCUBIC®), it was converted into a 2D cineloop that automatically scrolls in a continuous fashion. With STICLoop™, the image on the screen begins with the initial frame that was obtained by the mechanical probe, and there is automatic scrolling through all the frames until the last frame acquired in the sweep is reached. A cine rate of 8-12 loops/minute was used to evaluate the STIC volumes.

In one embodiment, STICLoop™ was used rather than manual navigation through multiplanar views as an aid to determine appropriateness of STIC volumes. The benefit of observing a 2D cineloop is that it allows an improved detection of problems (e.g. undulating movements), because it runs automatically at a constant speed. This contrasts to manual navigation through multiplanar views in which problems can be hidden or underestimated due to speed variability generated when a user operates the mouse. For example, if a fetus moves quickly back and forth during the STIC acquisition, a few frames could be displaced from the rest; however, this may not be as noticeable when manually navigating through multiplanar views, but is more likely to be detected using STICLoop™.

Some or all of the following criteria needed to be met in order to determine whether STIC volumes were appropriate: 1) fetal spine positioned between the 5- and 7-o'clock positions (minimizing the possibility of shadowing from the ribs or spine); 2) minimal or no motion artifacts observed (smooth sweep without evidence of abrupt jumps or discontinuous movements); 3) inclusion of the upper mediastinum as well as stomach; 4) minimal or absent shadowing that could obscure visualization of cardiac anatomy; 5) adequate image quality; 6) sequential axial planes parallel to each other, similar to a loaf of bread (i.e. absence of "drifting" spine); 7) absence of azimuth issues (atria/ventricles not appearing foreshortened in the four-chamber view); and 8) presence of the cardiac view (e.g. left ventricular outflow tract) within the STIC volume, as determined using 4D View which is available from GE Healthcare of Waukesha, Wis., USA. In one embodiment, all of the above criteria need to be met using the STICLoop in order to determine whether STIC volumes were appropriate. An additional criteria for determining if a STIC volume was appropriate is observing minimal or no motion artifacts in the sagittal plane. In one embodiment, this was observed or studied after pressing the initiate "all" button, 50% speed in Auto Cine in the 4D View product.

Finally, we tested the FINE method in four fetuses with congenital heart defects with postnatal confirmation (by postnatal echocardiography, surgery, or autopsy) to determine whether abnormal anatomy could be identified. The cases consisted of: coarctation of aorta (n=1; 25 weeks' gestation), tetralogy of Fallot (n=1; 25 weeks' gestation), transposition of great vessels (n=1; 28 weeks' gestation), and pulmonary atresia with intact ventricular septum (n=1; 29 weeks' gestation).

Examples

The seven anatomical structures within the heart (FIG. 1) chosen for marking in Anatomic Box® were: 1) cross-section aorta at level of stomach; 2) cross-section aorta at level of four-chamber view; 3) crux; 4) right atrial wall; 5) pulmonary valve; 6) cross-section superior vena cava; and 7) transverse aortic arch. From 50 STIC volume datasets, testing of the FINE method involved evaluating the 450 diagnostic planes (50 STIC volumes×9), and 450 VIS-Assistance™ AVI clips (50 STIC volumes×9), for a total of 900 images.

Visualization Rates for Fetal Echocardiography Views in Normal Fetuses

In the development phase (51 STIC volumes), the FINE method was able to generate nine fetal echocardiography views (Table 1) using: 1) diagnostic planes in 73-100% of cases; 2) VIS-Assistance in 98-100% of cases; and 3) a combination of diagnostic planes and/or VIS-Assistance in 98-100% of cases. In the testing phase (50 STIC volumes), the FINE method was able to generate nine fetal echocardiography views (Table 2) using: 1) diagnostic planes in 78%-100%; 2) VIS-Assistance in 98-100% of cases; and 3) combination of diagnostic planes and/or VIS-Assistance® in 98-100%. Adequacy of a given cardiac view was compared with the "gold standard" (image obtained by expert manual navigation of the STIC volume (4D View). An example of VIS-Assistance of the 3VT is illustrated in a normal fetus at 19.6 weeks' gestation, in which the 3VV and pulmonary valve are also shown.

TABLE 1

Development Phase of Fetal Intelligent Navigation Echocardiography (FINE): success rates of obtaining nine fetal echocardiography views after applying intelligent navigation to 51 normal spatiotemporal image correlation (STIC) volume datasets using diagnostic planes and/or Virtual Intelligent Sonographer Assistance (VIS-Assistance ®)

| Fetal echocardiography view | Diagnostic plane alone (n = 51) | | VIS-Assistance ® alone (n = 51) | | Diagnostic plane and/or VIS-Assistance ® (n = 51) | |
|---|---|---|---|---|---|---|
| | n (%) | 95% CI* | n (%) | 95% CI* | n (%) | 95% CI* |
| 1. Four-chamber | 47 (92) | 81 to 97 | 51 (100) | 92 to 100 | 51 (100) | 92 to 100 |
| 2. Five-chamber | 47 (92) | 81 to 97 | 51 (100) | 92 to 100 | 51 (100) | 92 to 100 |
| 3. LVOT | 45 (88) | 76 to 95 | 51 (100) | 92 to 100 | 51 (100) | 92 to 100 |
| 4. Short axis view of great vessels/RVOT | 42 (82) | 70 to 91 | 51 (100) | 92 to 100 | 51 (100) | 92 to 100 |
| 5. 3VT | 44 (86) | 74 to 94 | 50 (98) | 89 to >99.9 | 50 (98) | 89 to >99.9 |
| 6. Abdomen/Stomach | 51 (100)† | 92 to 100 | 51 (100)‡ | 92 to 100 | 51 (100) | 92 to 100 |
| 7. Ductal arch | 37 (73) | 59 to 83 | 51 (100) | 92 to 100 | 51 (100) | 92 to 100 |
| 8. Aortic arch | 44 (86) | 74 to 94 | 51 (100) | 92 to 100 | 51 (100) | 92 to 100 |
| 9. SVC/IVC | 41 (80) | 67 to 89 | 51 (100) | 92 to 100 | 51 (100) | 92 to 100 |
| SVC | 47 (92) | 81 to 97 | — | — | — | — |
| IVC | 43 (84) | 72 to 92 | — | — | — | — |

*The Wald method was used to calculate two-sided confidence intervals for proportions expressed in the table; as the true proportion cannot exceed 100%, upper confidence limits are truncated at 100%.

†Defined as visualization of the stomach in the diagnostic plane

‡Defined as visualization of both the stomach and four-chamber view in VIS-Assistance ® (to determine situs)

3VT, three-vessels and trachea,

IVC, inferior vena cava;

LVOT, left ventricular outflow tract;

RVOT, right ventricular outflow tract;

SVC, superior vena cava.

For each cardiac volume dataset (n=50), the number of fetal echocardiography views that were successfully obtained through diagnostic planes or VIS-Assistance® was also calculated (Table 3). For diagnostic planes, 76% (n=38) of volume datasets demonstrated either eight (36%; n=18) or all nine (40%; n=20) echocardiography views, while 18% (n=9) demonstrated seven views. For VIS-Assistance®, all nine fetal echocardiography views were obtained in 94% (n=47) of volume datasets, while 6% (n=3) of datasets demonstrated eight views.

TABLE 3

Number of fetal echocardiography views successfully obtained through diagnostic planes or Virtual Intelligent Sonographer Assistance (VIS-Assistance ®) for each normal spatiotemporal image correlation (STIC) volume dataset (n = 50)

| Number of fetal echocardiography views successfully obtained for each normal STIC volume dataset (n = 9 maximum) | Diagnostic planes (n = 50) | | Virtual Intelligent Sonographer Assistance (VIS-Assistance ®) (n = 50) | |
|---|---|---|---|---|
| | n | % | n | % |
| 5 | 1 | 2 | — | — |
| 6 | 2 | 4 | — | — |
| 7 | 9 | 18 | — | — |
| 8 | 18 | 36 | 3 | 6 |
| All 9 views obtained | 20 | 40 | 47 | 94 |
| TOTAL | 50 | 100 | 50 | 100 |

TABLE 2

Testing Phase of Fetal Intelligent Navigation Echocardiography (FINE): success rates of obtaining nine fetal echocardiography views after applying intelligent navigation to 50 normal spatiotemporal image correlation (STIC) volume datasets using diagnostic planes and/or Virtual Intelligent Sonographer Assistance (VIS-Assistance ®)

| Fetal echocardiography view | Diagnostic plane alone (n = 50) | | VIS-Assistance ® alone (n = 50) | | Diagnostic plane and/or VIS-Assistance ® (n = 50) | |
|---|---|---|---|---|---|---|
| | n (%) | 95% CI* | n (%) | 95% CI* | n (%) | 95% CI* |
| 1. Four-chamber | 48 (96) | 86 to 100 | 50 (100) | 92 to 100 | 50 (100) | 92 to 100 |
| 2. Five-chamber | 48 (96) | 86 to 100 | 50 (100) | 92 to 100 | 50 (100) | 92 to 100 |
| 3. LVOT | 45 (90) | 78 to 96 | 49 (98) | 89 to >99.9 | 49 (98) | 89 to >99.9 |
| 4. Short axis view of great vessels/RVOT | 42 (84) | 71 to 92 | 50 (100) | 92 to 100 | 50 (100) | 92 to 100 |
| 5. 3VT | 46 (92) | 81 to 97 | 50 (100) | 92 to 100 | 50 (100) | 92 to 100 |
| 6. Abdomen/Stomach | 50 (100)† | 92 to 100 | 49 (98)‡ | 89 to >99.9 | 50 (100) | 92 to 100 |
| 7. Ductal arch | 39 (78) | 65 to 87 | 49 (98) | 89 to >99.9 | 49 (98) | 89 to >99.9 |
| 8. Aortic arch | 45 (90) | 78 to 96 | 50 (100) | 92 to 100 | 50 (100) | 92 to 100 |
| 9. SVC/IVC | 41 (82) | 69 to 90 | 50 (100) | 92 to 100 | 50 (100) | 92 to 100 |
| SVC | 46 (92) | 81 to 97 | — | — | — | — |
| IVC | 43 (86) | 74 to 93 | — | — | — | — |

*The Wald method was used to calculate two-sided confidence intervals for proportions expressed in the table; as the true proportion cannot exceed 100%, upper confidence limits are truncated at 100%.
†Defined as visualization of the stomach in the diagnostic plane
‡Defined as visualization of both the stomach and four-chamber view in VIS-Assistance ® (to determine situs)
3VT, three-vessels and trachea;
IVC, inferior vena cava;
LVOT, left ventricular outflow tract;
RVOT, right ventricular outflow tract;
SVC, superior vena cava.

Comments About Diagnostic Planes in Normal Fetuses

After the crux is marked by the user, the right atrial wall is marked next by using an angled line that is traced over the ventricular septum by the user. However, if the left ventricular outflow tract was not successfully obtained in the diagnostic plane, we designed an alternative straight line to mark the atrial wall, which occurred in 30% (n=15) of cases. By using an initial angled line and then a straight line when applicable, the left ventricular outflow tract diagnostic plane was successfully obtained in 90% (n=45) cases. It is noteworthy, however, that even when using the initial angled line to mark the right atrial wall, VIS-Assistance still successfully demonstrated the left ventricular outflow tract in 98% (n=49) of cases.

Comments about VIS-Assistance in Normal Fetuses

One of the advantages of the four-chamber view VIS-Assistance is that it enables the operator to visualize the atrial septum and pulmonary veins.

When compared to the four-chamber view diagnostic plane, the atrial septum was seen (or more clearly seen) in 94% (n=47) of cases in the VIS-Assistance®. In the other 6% (n=3) of cases, however, the septum secundum was still successfully visualized in the five-chamber view diagnostic plane. It is noteworthy that pulmonary veins were successfully visualized in 96% (n=48) of cases in the four-chamber view VIS-Assistance, and not visualized in only 2 cases. However, in the latter, this was successfully seen in the five-chamber view VIS-Assistance. For the abdomen/stomach VIS-Assistance™, both the stomach and four-chamber view were visualized in 98% (n=49) of cases so that situs could be determined.

One of the objectives of VIS-Assistance is to provide more information about the diagnostic plane and/or its surroundings. For example, a fetus at 32.4 weeks' gestation in which the left ventricle in the five-chamber view diagnostic plane appears foreshortened, and there is a question as to whether this is due to a titled plane (azimuth), or because the left ventricle is truly hypoplastic. By activating VIS-Assistance, it became clear the left ventricle was not hypoplastic, and the apparent small ventricle was due to an azimuth effect.

FINE Method in Four Cases of Congenital Heart Defects
Coarctation of Aorta

The FINE method is illustrated in 1 case of coarctation of aorta (25 weeks' gestation). For Case 1, the following abnormalities were seen: 1) 3VT view: narrow transverse aorta; 2) four chamber view: left ventricle smaller (vs. right ventricle) but still apex-forming; normal movement of mitral valve; 3) left ventricular outflow tract: narrow as seen on VIS-Assistance®; and 4) short axis view of great vessels/right ventricular outflow tract: small cross-section of aorta. The aortic arch view clearly demonstrated the coarctation.
Tetralogy of Fallot In this fetus with tetralogy of Fallot at 25 weeks' gestation with mild pulmonary stenosis, 6 cardiac views were abnormal, demonstrating the typical features of this cardiac abnormality: 1) 3VT: pulmonary stenosis; 2) four-chamber view: appeared normal in the diagnostic plane; however, VIS-Assistance® demonstrated the ventricular septal defect; 3) five-chamber view: overriding aorta and ventricular septal defect; 4) left ventricular outflow tract: overriding aorta and ventricular septal defect; 5) short axis view of great vessels/right ventricular outflow tract: pulmonary stenosis, dilated aorta in cross-section, tortuous ductus arteriosus; and 6) difficulty in visualizing a normal ductal arch in diagnostic plane and VIS-Assistance.
Transposition of Great Vessels This fetus at 28 weeks' gestation is an example when anatomical structures cannot be successfully marked using the Anatomic Box® feature due to the presence of obvious congenital heart disease. During the marking process, the four-chamber view appeared normal; however, marking the "pulmonary valve" (which was actually the true aortic valve) and transverse aortic arch was possible only for the same vessel. The true pulmonary artery (arising from the left ventricle) was not in the expected location for marking. Yet, it is noteworthy that the marking process was still relatively simple. The transposition of great vessels was demonstrated and five cardiac views were abnormal: 1) 3VT: aorta arising from right ventricle and superior vena cava in cross-section. VIS-Assistance demonstrated that another vessel (pulmonary artery) was present to the left of the aorta; 2) five-chamber view: while the diagnostic plane appeared normal, the great vessels arising parallel from the ventricles and side-by-side were seen in VIS-Assistance; 3) left ventricular outflow tract: great vessels arising parallel from the ventricles and side-by-side (pulmonary artery from left ventricle and aorta from right ventricle); 4) short axis view of great vessels/right ventricular outflow tract: pulmonary artery bifurcation was seen, but the cross-section of aorta was not (abnormal view); 5) ductal arch: appeared abnormal overall. The aorta arises anteriorly from the right ventricle ("hockey stick" orientation) while the pulmonary artery (confirmed by its bifurcation) is to the right of the aorta on the screen.

Pulmonary Atresia with Intact Ventricular Septum

In this fetus at 29 weeks' gestation, 6 cardiac views were abnormal and the pulmonary atresia was directly demonstrated in 3 views: 1) 3VT view: hypoplasia of pulmonary artery; 2) four-chamber view: small right ventricle and dilated right atrium (due to tricuspid regurgitation). VIS-Assistance confirmed that the right ventricle was truly small; 3) five-chamber view: small right ventricle small and dilated right atrium; 4) left ventricular outflow tract: dilated; 5) short axis view of great vessels/right ventricular outflow tract: hypoplasia of pulmonary artery; and 6) ductal arch: hypoplasia of pulmonary artery and tortuous ductus arteriosus connecting to descending aorta.

Discussion

The conventional method to analyze a cardiac volume dataset is using manual controls to interrogate the three orthogonal planes in the multiplanar display, in order to generate a set of standard planes required for prenatal diagnosis. Unfortunately, many operators examine the fetal heart without using a systematic approach. Thus, the effort is often time-consuming and error prone, because identification of adequate diagnostic planes is operator dependent. To address this, algorithms have been developed to systematically examine 3D/4D volume datasets, so that diagnostic planes can be retrieved with efficiency, speed, and accuracy.

FINE is a novel, simple, and automatic method and apparatus for visualization of nine standard fetal echocardiography views from dataset volumes obtained with STIC and applying intelligent navigation technology. Indeed, seven of the views have been recommended by the American Institute of Ultrasound in Medicine (AIUM) for the performance of fetal echocardiography. Also demonstrated is the five-chamber view, as well as the stomach to determine situs. The FINE method is different from previous methods, because it decreases substantially the number of manual steps to obtain the cardiac views, making it less operator-dependent. The user is only required to mark anatomical structures within the 2D sweep to trigger intelligent navigation. Moreover, in order to further improve the success of obtaining each cardiac view and provide more information about the view and its surrounding anatomical areas, we developed VIS-Assistance® which is operator independent. Table 4 further describes the characteristics and advantages of the FINE method.

Intelligent navigation is unique because: 1) there is no need to fit the heart into a pre-determined model to acquire diagnostic planes; 2) no manual manipulation is required (e.g. tilting, rotation); and 3) the user does not need to match diagnostic planes to a diagram. Moreover, because the technology generates a mathematical reconstruction of the organ of interest, the successful display of diagnostic planes can occur despite varying gestational ages, fetal positions, and anatomical variability (e.g. size of heart, cardiac axis, etc.).

TABLE 4

Characteristics of Fetal Intelligent Navigation Echocardiography (FINE) used to generate standard fetal echocardiography views

| Characteristic | FINE |
|---|---|
| 1. Gestational age | Second to third trimesters |
| 2. Ultrasound modality | Volumetric sonography (STIC datasets) |
| 3. Fetal echocardiography views | Nine views: Four chamber Five chamber Left ventricular outflow tract Short axis view of great vessels/right ventricular outflow tract Three vessels and trachea Abdomen/stomach Ductal arch Aortic arch Superior and inferior vena cava |
| 4. General characteristics | Intelligent navigation (vs. manual) Seven anatomical structures of fetal heart are marked using Anatomic Box ® to generate a geometrical model of the heart (i.e. parsimonious) System automatically and immediately rotates, aligns, dissects and scales volume dataset to display nine cardiac diagnostic planes simultaneously Automatic realignment of STIC volume, and reorientation and standardization of the anatomical position so that the fetus and diagnostic planes are consistently displayed in the same manner each time Method is predictable (i.e. diagnostic planes are generated in a consistent way) and adaptive ("fits" the anatomy of each particular case under examination) VIS-Assistance ® is available for each diagnostic plane |
| 5. Cardiac diagnostic planes | Successful display occurs despite different gestational ages and also in the presence of anatomical variability (e.g. cardiac axis and geometry) All nine planes are displayed simultaneously in a single template |
| 6. VIS-Assistance ® | Operator-independent sonographic navigation and exploration of surrounding structures in a cardiac diagnostic plane of interest ("virtual" sonographer) |
| 7. Labeling | Automatic (fetal echocardiography views, anatomical structures, left and right side of fetus, and cranial and caudal ends) Labeling stays with the corresponding anatomical structure(s), even as the image is increased in size (zoom) |
| 8. Cardiac phase recognition | Facilitates marking of anatomical structures (e.g. closed pulmonary valve) and is an important feature to increase the success of obtaining echocardiography views |
| 9. Other characteristics | STICLoop ™ (evaluation of STIC volume to determine its appropriateness before applying the FINE method) |
| 10. Technical aspects | Can operate on conventional computers; is not dependent on specific ultrasound platforms or on the use of software to perform manual navigation of volume datasets |

TABLE 4-continued

Characteristics of Fetal Intelligent Navigation Echocardiography
(FINE) used to generate standard fetal echocardiography views

| Characteristic | FINE |
|---|---|
| 11. Telemedicine | STIC Volume datasets, diagnostic planes, and VIS-Assistance ® video clips can be transmitted Smartphones, tablets and other devices may also be used to receive the transmitted information (diagnostic planes or VIS-Assistance ® video clips) |

STIC, spatiotemporal image correlation;
VIS-Assistance ®, Virtual Intelligent Sonographer Assistance Marking anatomical structures in different planes of the heart using intelligent navigation allows inferences of the anatomical relationships in multiple dimensions (generating a mathematical reconstruction of the heart). Thus, the successful display of diagnostic planes can occur over a wide range of gestational ages, fetal positions, and in the presence of anatomic variations. The FINE method and apparatus is fundamentally different from previously described techniques, because it does not depend on manipulation of the image size to fit a pre-determined model of the heart, manual standardization or manipulation of the STIC volume dataset or reference planes, and does not depend on tomographic ultrasound imaging (TUI) technology. TUI allows volume datasets to be automatically sliced, displaying parallel multiple images that are fixed and equidistant to each other.

Importance of Obtaining an Appropriate STIC Volume Dataset

Acquiring an appropriate STIC volume is essential for its successful display and analysis. Factors that interfere with image quality in conventional two-dimensional sonography (e.g. early gestational age, fetal positioning, maternal body habitus) will also affect STIC quality. It is important to stress that the FINE method may not be successful in generating fetal echocardiographic views if: the quality of the STIC volume dataset is inadequate (e.g motion artifact), the volume does not contain information about the cardiac views, the STIC acquisition was not acquired from a true four-chamber view (e.g. true cross-section of the thorax, proper alignment in the axial plane), and the user does not mark the anatomical structures appropriately (due to poor visualization, abnormal anatomy, etc.). Therefore, proper acquisition of STIC volume datasets is essential in order to perform the FINE method, and we proposed the use of STICLoop™ as a tool to determine the appropriateness of such volumes. Acquisition protocols that include more than one volume increase the chances that relevant information can be obtained. Thus, further STIC acquisitions should be obtained if the volumes are not appropriate.

Indications for the FINE Method

The FINE method can also be used as an aid for examination of the fetal heart in the population at large, rather than to diagnose specific congenital heart defects. Since an optimal fetal position can change during the course of a sonographic examination, it may be prudent to acquire a STIC volume when the position is optimal, and then proceed to two-dimensional sonography. If the latter is unsuccessful, the STIC volume is available for examination and analysis. We acknowledge that our method may not be useful in cases of certain congenital heart defects, since the abnormality may already be obvious in the four-chamber view (e.g. hypoplastic left heart, atrioventricular canal defect) or since anatomical structures may either not be present for marking or are not in the usual location (e.g. truncus arteriosus). Indeed, if the anatomical structures that we have pre-specified cannot be successfully marked using the Anatomic Box® feature, this may be due to: 1) suboptimal STIC quality with poor visualization; 2) lack of familiarity with landmarks; or 3) the presence of congenital heart disease. In such cases, patients should undergo real-time sonographic examination of the fetal heart by an expert. The FINE method may have value, however, in the presence of certain types of congenital heart defects: 1) those which may not be directly obvious in axial views of the heart (e.g. coarctation of aorta, aortic/pulmonary stenosis, ventricular septal defect) and require other cardiac views for diagnosis; and 2) in cases where VIS-Assistance® provides further anatomical information that may not have been obtained with two-dimensional scanning (e.g. evaluation for pulmonary veins in the four-chamber view in the case of anomalous pulmonary venous return). Moreover, the simultaneous display of cardiac defects in multiple views may also be informative (e.g. pulmonary stenosis visualized in 3VVT, right ventricular outflow tract, and ductal arch views).

When the FINE method was used to examine 4 fetuses with known congenital heart disease, abnormalities were identified in the planes/VISA. We were particularly interested in evaluating a set of cases in which the anomaly was not obvious. For example, for the one case of coarctation (a difficult diagnosis to make prenatally), the aortic arch view successfully demonstrated the abnormality in both the diagnostic plane and VIS-Assistance. For other cardiac defects (e.g. tetralogy of Fallot), it was advantageous to examine multiple cardiac views, because the abnormality could be confirmed more easily (e.g. overriding aorta and ventricular septal defect in the left ventricular outflow tract and five-chamber views, and pulmonary stenosis in right ventricular outflow tract, 3VT views).

Limitations of Intelligent Navigation

Application of this technology and the FINE method are not designed to replace the performance of real-time fetal echocardiography, since only the latter can evaluate cardiac rate or rhythm disturbances, cardiac function, Doppler velocimetry, etc. at the present time.

Future of Intelligent Navigation and Conclusions

One strategy to improve the prenatal detection of congenital heart defects is the use of volume sonography and internet consultation. Sonographers do not have to be specifically experienced in three- or four-dimensional sonography to acquire high quality STIC volumes. Moreover, STIC acquisitions are feasible and when acquired by general obstetricians, they can subsequently be evaluated by a fetal echocardiologist for prenatal confirmation of normal cardiac structures or exclusion of major cardiac malformations. Cardiac examination from STIC volumes has also been shown to have high intra- and interobserver repeatability in each trimester of pregnancy. Among centers with expertise, 4D sonography has been shown to be an accurate and reliable technique for fetal echocardiography, since STIC volumes contain sufficient information to distinguish normal and abnormal fetal hearts, identify structural anomalies, and accurately diagnose specific heart defects. Therefore, STIC volume datasets can be sent via the Internet to experts where standard views for fetal echocardiography can be obtained from these volumes.

Internet consultation for fetal cardiac sonography, however, is time consuming and requires dedicated software. An important advantage of intelligent navigation technology is that it operates on conventional computers, and is not tied to specific ultrasound machines or post-processing software used to manually navigate volume datasets. Thus, STIC volume datasets, diagnostic planes, and VIS-Assistance video clips from the FINE method may be transmitted by telemedicine to a consultant for evaluation and expert opinion. Smart phones and tablets may also access this transmitted information from any location, as long as internet access is available. Since the FINE method demonstrates fetal cardiac diagnostic planes and there is spontaneous navigation around each of the planes (VIS-Assistance) automatically, this decreases operator dependency and the time spent by the expert consultant as well. While a user may be able to acquire a STIC volume dataset and mark the anatomical structures using Anatomic Box® easily, one may not have the expertise to interpret and render an opinion based on the resulting diagnostic planes and/or VIS-Assistance. Therefore, the advantage of this technology is that a consultant may be able to perform this from a distance and render an expert opinion.

The introduction of novel methods, such as the one proposed herein, may simplify examination of the fetal heart and reduce operator dependency. Moreover, it has the potential to improve the efficiency and workflow of fetal echocardiography by reducing the time necessary to obtain standard cardiac views. Using the FINE method, inability to obtain expected views or the appearance of abnormal views in the generated planes or VIS-Assistance should raise the index of suspicion for congenital heart disease.

Figure 2:
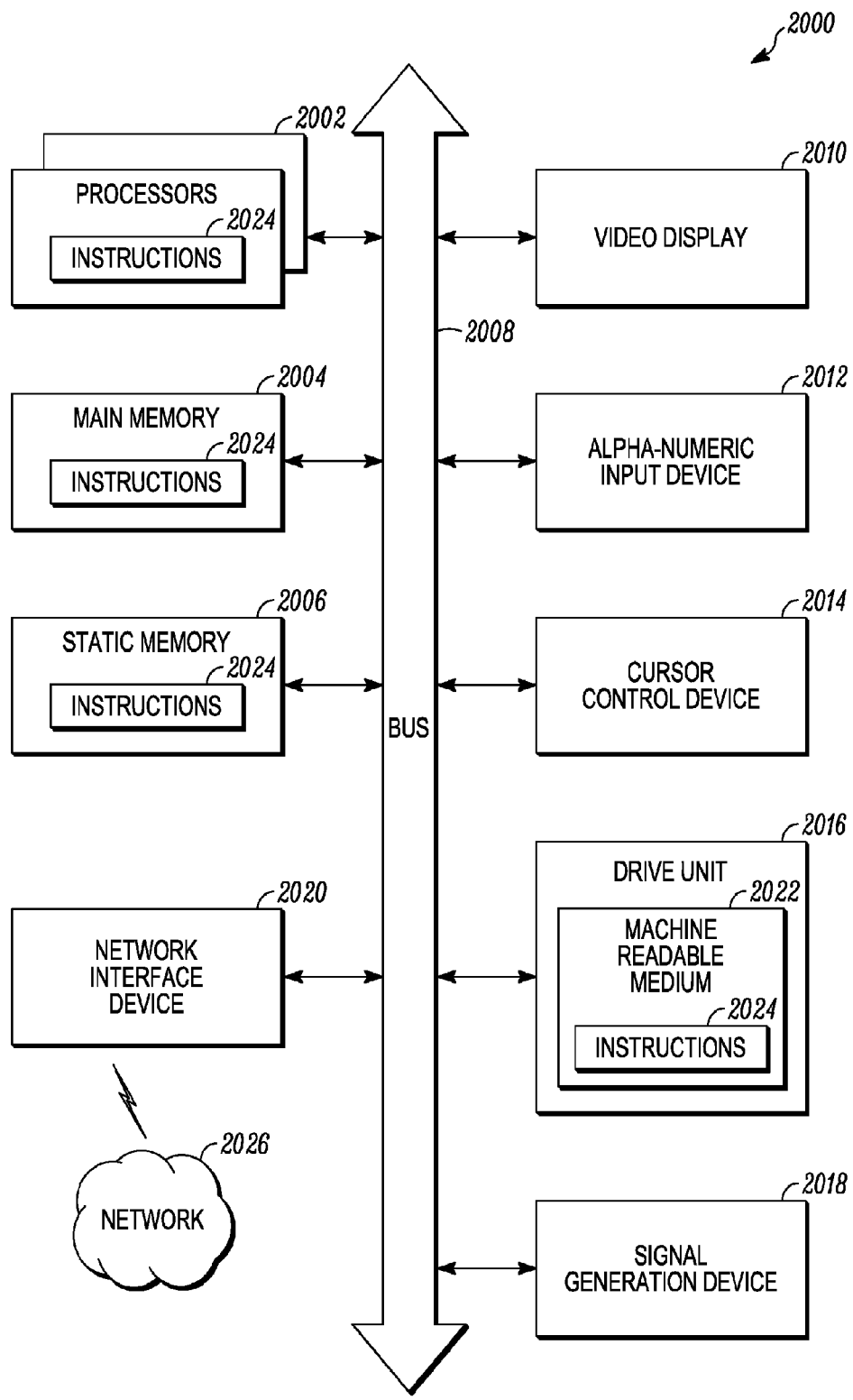
FIG. 2 shows a schematic diagram of a computer system used in the system for driving business, according to an example embodiment.

FIG. 2 shows a diagrammatic representation of a computing device for a machine in the example electronic form of a computer system 2000, within which a set of instructions for causing the machine to perform any one or more of the error correction methodologies discussed herein can be executed or is adapted to include the apparatus for error correction as described herein. In various example embodiments, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a personal computer (PC), a tablet PC, a set-top box (STB), a Personal Digital Assistant (PDA), a cellular telephone, a portable music player (e.g., a portable hard drive audio device such as a Moving Picture Experts Group Audio Layer 3 (MP3) player, a web appliance, a network router, a switch, a bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 2000 includes a processor or multiple processors 2002 (e.g., a central processing unit (CPU), a graphics processing unit (GPU), arithmetic logic unit or all), and a main memory 2004 and a static memory 2006, which communicate with each other via a bus 2008. The computer system 2000 can further include a video display unit 2010 (e.g., a liquid crystal display (LCD) or a cathode ray tube (CRT)). The computer system 2000 also includes an alphanumeric input device 2012 (e.g., a keyboard), a cursor control device 2014 (e.g., a mouse), a disk drive unit 2016, a signal generation device 2018 (e.g., a speaker) and a network interface device 2020.

The disk drive unit 2016 includes a computer-readable medium 2022 on which is stored one or more sets of instructions and data structures (e.g., instructions 2024) embodying or utilized by any one or more of the methodologies or functions described herein. The instructions 2024 can also reside, completely or at least partially, within the main memory 2004 and/or within the processors 2002 during execution thereof by the computer system 2000. The main memory 2004 and the processors 2002 also constitute machine-readable media.

The instructions 2024 can further be transmitted or received over a network 2026 via the network interface device 2020 utilizing any one of a number of well-known transfer protocols (e.g., Hyper Text Transfer Protocol (HTTP), CAN, Serial, or Modbus).

While the computer-readable medium 2022 is shown in an example embodiment to be a single medium, the term "computer-readable medium" should be taken to include a single medium or multiple media (e.g., a centralized or distributed database, and/or associated caches and servers) that store the one or more sets of instructions and provide the instructions in a computer readable form. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, tangible forms and signals that can be read or sensed by a computer. Such media can also include, without limitation, hard disks, floppy disks, flash memory cards, digital video disks, random access memory (RAMs), read only memory (ROMs), and the like.

FIG. 3 is a flow diagram associated with a computerized method 300, according to an example embodiment. The computerized method 300 includes obtaining an image of the heart 310, placing markers on certain of the images of the heart 312 and determining their relative position to one another 314 and using the relative positions to generate selected views of the heart 316. The selected views of the heart can be orientated for analysis when rendered on a display or screen. Of course, this method is not limited to images of the heart. It is contemplated that the method can also be applied to other body portions. When the computerized method 1200, discussed above, is programmed into a memory of a general purpose computer, the computer and instructions form a special purpose machine. The instructions, when programmed into a memory of a general purpose computer, are in the form of a non transitory set of instructions.

The example embodiments described herein can be implemented in an operating environment comprising computer-executable instructions (e.g., software) installed on a computer, in hardware, or in a combination of software and hardware. Modules as used herein can be hardware or hardware including circuitry to execute instructions. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software programs for implementing the present method(s) can be written in any number of suitable programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Perl, UNIX Shell, Visual Basic or Visual Basic Script, Virtual Reality Markup Language (VRML), ColdFusion™ or other compilers, assemblers, interpreters or other computer languages or platforms.

Figure 4:
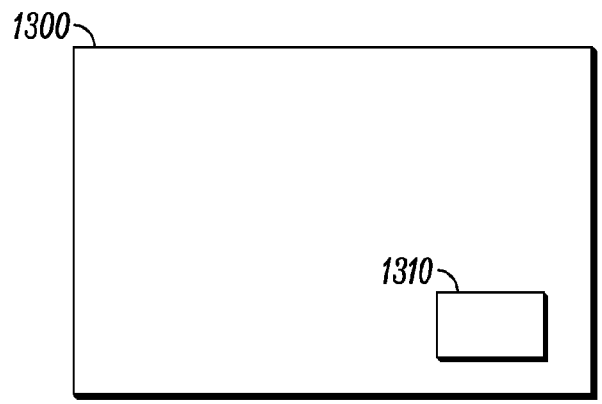
FIG. 4 is a schematic drawing of a machine readable medium that includes an instruction set, according to an example embodiment.

FIG. 4 is a schematic drawing of a machine readable medium 1300 that includes an instruction set 1310, according to an example embodiment. The machine-readable medium 1300 that provides instructions 1310 that, when executed by a machine, cause the machine to perform operations including of the above described methods. The machine readable medium 1300 also includes instructions that, when executed by a machine, cause the machine to perform operations that include receiving an input related to prompt displayed on a recycling container, identifying a marketing opportunity associated with the prompt, identifying the source of the received input, and sending the marketing opportunity to the source. A machine readable medium includes an instruction set. The instruction set, when executed by a machine, causes a machine to perform operations that include obtaining a dataset volume of a heart using spatio-temporal image correlation in an ultrasound imaging mode, marking a plurality of anatomical points of the heart within the obtained dataset, and generating a plurality of diagnostic images of the heart from the marked anatomical points of the heart from the obtained dataset. The instruction set, when executed by a machine, also causes a machine to perform operations to mark at least two of the following anatomical portions of the heart: an aorta point in a cross-section of the aorta at level of stomach; an aorta point in cross-section of the aorta at level of the four chamber view of the heart; a crux point in a view of the cross-section of the aorta at level of the four chamber view of the heart; a line through the ventricular septum, the crux point, and terminating at the right atrial wall of the heart; a pulmonary valve point substantially in the middle of the pulmonary valve of the heart; a superior vena cava point substantially in the middle of the superior vena cava of the heart; and a transverse aortic arch point. The instruction set, when executed by a machine, also causes a machine to perform operations that includes presenting a sample view of a sample heart with a marked anatomical portion, and presenting a similar view of the heart from the obtained data set. The instruction set also prompts a response for marking the heart from the obtained data set. The instruction set, when executed by a machine, causes a machine to perform operations to substantially immediately generate at least a plurality of the following fetal echocardiography views: a four-chamber view; a five-chamber view; a left ventricular outflow tract view; a short axis view of great vessels/right ventricular outflow tract view; a three-vessels and trachea view; an abdomen/stomach view; a ductal arch view; an aortic arch view; or a superior and inferior vena cava view.

The machine is capable of carrying out the following methods based on an instruction that sets forth the method. An imaging method includes obtaining a dataset volume of a heart using spatio-temporal image correlation in an ultrasound imaging mode, marking a plurality of anatomical points of the heart within the obtained dataset, and generating a plurality of diagnostic images of the heart from the marked anatomical points of the heart in the obtained dataset. Marking the plurality of the anatomical points of the heart includes marking at least a plurality of the following anatomical points of the heart: an aorta point in a cross-section of the aorta at level of stomach; an aorta point in cross-section of the aorta at level of the four chamber view of the heart; a crux point in a view of the cross-section of the aorta at level of the four chamber view of the heart; a line through the ventricular septum, the crux point, and terminating at the right atrial wall of the heart; a pulmonary valve point substantially in the middle of the pulmonary valve of the heart; a superior vena cava point substantially in the middle of the superior vena cava of the heart; and a transverse aortic arch point. In one embodiment, the imaging method also includes marking at least one line corresponding to anatomical portions of the heart. In another embodiment, all of the marks are made on the image of the captured data of the heart. Marking the plurality of the anatomical points of the heart, in some embodiments, includes presenting a sample view of a sample heart with a marked anatomical portion, presenting a similar view of the heart from the obtained data set, and prompting a response for marking the heart from the obtained data set. In one embodiment, marking the plurality of the anatomical points of the heart further comprises labeling an anatomical point in response to receiving a response for marking the heart. The label or labels are displayed on a computer monitor. A plurality of the anatomical points of the heart can be marked in the same or a similar way and also labeled and displayed after placing the mark on the obtained data set. In one embodiment, a plurality of sample views of a sample heart marked at an anatomical portion are presented. A plurality of unmarked views of the heart from the obtained data set that correspond to the plurality of sample views are also presented. A response for marking the plurality of unmarked views of the heart from the obtained data set is prompted, and a plurality of diagnostic images from a plurality of marks received as responses are generated. In one embodiment of the imaging method a marked view of the heart from the obtained data set is reoriented upon detecting a fetal heart from a baby in a breech presentation. A warning note is displayed, in some embodiments, indicating that the baby is in a breech presentation. The warning note includes a prompt seeking a response that the reorientation action is acceptable. In still another embodiment, the imaging method includes adjusting at least one of the generated diagnostic views by changing the angle of at least one of the generated diagnostic views. In one embodiment, the generated diagnostic views are in planes. Adjusting includes a set of steps for changing the view slightly to get a better view of the area of interest. In one embodiment, a computer is able to conduct an adjustment. A computer generally makes these adjustments as a set of predetermined steps. In some embodiments, adjusting at least one of the generated diagnostic views shifts the diagnostic view to a parallel plane within the dataset volume and in another embodiment, the angle of the view may be changed. In still another embodiment, both of these actions can be taken to effectuate the adjustment. Generating a plurality of diagnostic images of the heart from the marked anatomical points of the heart from the obtained dataset includes using information from at least two of the marked anatomical points in a decision tree to determine the plane of diagnostic image. The information is placed in a decision tree. A series of "yes" or "no" type questions are answered. The outcome is used to generate the diagnostic view. The generated plurality of diagnostic images are displayed on a computer display. The plurality of diagnostic images generated from the obtained dataset includes at least a plurality of the following fetal echocardiography views: a four-chamber view; a five-chamber view; a left ventricular outflow tract view; a short axis view of great vessels/right ventricular outflow tract view; a three-vessels and trachea view; an abdomen/stomach view; a ductal arch view; an aortic arch view; and a superior and inferior vena cava view.

The present disclosure refers to instructions that are received at a memory system. Instructions can include an operational command, e.g., read, write, erase, refresh and the like, an address at which an operational command should be performed; and the data, if any, associated with a command. The instructions can also include error correction data.

This has been a detailed description of some exemplary embodiments of the invention(s) contained within the disclosed subject matter. Such invention(s) may be referred to, individually and/or collectively, herein by the term "invention" merely for convenience and without intending to limit the scope of this application to any single invention or inventive concept if more than one is in fact disclosed. The detailed description refers to the accompanying drawings that form a part hereof and which shows by way of illustration, but not of limitation, some specific embodiments of the invention, including a preferred embodiment. These embodiments are described in sufficient detail to enable those of ordinary skill in the art to understand and implement the inventive subject matter. Other embodiments may be utilized and changes may be made without departing from the scope of the inventive subject matter. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of examining fetal hearts and identifying normality or abnormality of fetal hearts, comprising:
   obtaining spatiotemporal image correlation ultrasound data of a fetal heart of a subject to generate a plurality of fetal heart images at different cardiac phases;
   displaying different marked sample images of a sample fetal heart and at respective cardiac phases, the different marked sample images each marking a different feature of the sample fetal heart at a respective marked location;
   sequentially presenting one of the different marked sample images to a user along with one of the fetal heart images;
   as each of the different marked sample images is sequentially presented, prompting the user to mark the different feature in a respective fetal heart image based on its marked location in the different marked sample image, to create a plurality of marked fetal heart images;
   reconstructing a unique geometric model of the fetal heart based on the marked fetal heart images, from which fetal echocardiography views can be extracted; and
   displaying the fetal echocardiography views of the fetal heart.

2. The method of claim 1, wherein sequentially presenting one of the different marked sample images to the user further includes presenting at least one marked sample image and corresponding fetal heart image for marking that includes marking outside a four-chamber view.

3. The method of claim 1, wherein sequentially presenting one of the different marked sample images to the user along with one of the fetal heart images includes presenting in a specific order.

4. The method of claim 3, wherein the one of the different marked sample images sequentially presented to the user along with the one of the fetal heart images includes seven anatomical structures of the fetal heart in the order of:
   1) aorta at a stomach level;
   2) aorta at a level of a four-chamber view;
   3) a crux at a level of the four-chamber view;
   4) a right atrial wall at a level of the four-chamber view;
   5) a pulmonary valve;
   6) a superior vena cava; and
   7) a transverse aortic arch.

5. The method of claim 1, further comprising prompting the user to mark three different features of one of the fetal heart images.

6. The method of claim 5, wherein the one fetal heart image marked with the three different feature includes markings of a location of an aorta, a location of a crux, and a location of a right atrial wall.

7. The method of claim 1, wherein displaying the fetal echocardiography views of the fetal heart further includes displaying the fetal echocardiography views simultaneously in a single display to the user.

8. A machine readable medium that includes an instruction set, the instruction set, when executed by a machine, causing a machine to perform operations comprising:
   obtaining spatiotemporal image correlation ultrasound data of a fetal heart of a subject to generate a plurality of fetal heart images at different cardiac phases;
   showing different marked sample images of a sample fetal heart and at respective cardiac phases, the different marked sample images each marking a different feature of the sample fetal heart at a respective marked location;
   sequentially presenting one of the different marked sample images to a user along with one of the fetal heart images, the one fetal heart image selected based on the one of the different marked sample images;
   as each of the different marked sample images is sequentially presented, prompting the user to mark the different feature in a respective fetal heart image based on its marked location in the different marked sample image, to create a plurality of marked fetal heart images;
   reconstructing a unique geometric model of the fetal heart based on the marked fetal heart images, from which fetal echocardiography views can be extracted; and
   displaying the fetal echocardiography views of the fetal heart.

9. The machine readable medium that includes the instruction set of claim 8, wherein the instruction set, when executed by the machine, causes the machine to perform operations including sequentially presenting one of the different marked sample images to the user further includes presenting at least one marked sample image and corresponding fetal heart image for marking that includes marking outside a four-chamber view.

10. The machine readable medium that includes the instruction set of claim 8, wherein the instruction set, when executed by the machine, causes the machine to perform operations including sequentially presenting one of the different marked sample images to the user along with one of the fetal heart images includes presenting in a specific order.

11. The machine readable medium that includes the instruction set of claim 10, wherein the one of the different marked sample images sequentially presented to the user along with the one of the fetal heart images includes seven anatomical structures of the fetal heart in the order of:
   1) aorta at a stomach level;
   2) aorta at a level of a four-chamber view;

3) a crux at a level of the four-chamber view;
4) a right atrial wall at a level of the four-chamber view;
5) a pulmonary valve;
6) a superior vena cava; and
7) a transverse aortic arch.

12. The machine readable medium that includes the instruction set of claim 8, wherein the instruction set, when executed by the machine, causes the machine to perform operations including prompting the user to mark three different features of one of the fetal heart images.

13. The machine readable medium that includes the instruction set of claim 12, wherein the one fetal heart image marked with the three different feature includes markings of a location of an aorta, a location of a crux, and a location of a right atrial wall.

14. The machine readable medium that includes the instruction set of claim 8, wherein displaying the fetal echocardiography views of the fetal heart further includes displaying the fetal echocardiography views simultaneously in a single display to the user.

15. An imaging system, comprising:
a processor that executes an instruction set that causes a computing system to perform operations comprising:
obtaining spatiotemporal image correlation ultrasound data of a fetal heart of a subject to generate a plurality of fetal heart images at different cardiac phases;
showing different marked sample images of a sample fetal heart and at respective cardiac phases, the different marked sample images each marking a different feature of a sample fetal heart at a respective marked location;
sequentially presenting one of the different marked sample images to a user along with one of the fetal heart images;
as each of the different marked sample images is sequentially presented, prompting the user to mark the different feature in a respective fetal heart image based on its marked location in the different marked sample image, to create a plurality of marked fetal heart images;
reconstructing a unique geometric model of the fetal heart based on the marked fetal heart images, from which fetal echocardiography views can be extracted; and
displaying the fetal echocardiography views of the fetal heart.

16. The imaging system of claim 15, wherein the processor executes an instruction that causes the computing system to perform operations including sequentially presenting one of the different marked sample images to the user further includes presenting at least one marked sample image and corresponding fetal heart image for marking that includes marking outside of a four-chamber view.

17. The imaging system of claim 15, wherein the processor executes an instruction that causes the computing system to perform operations including sequentially presenting one of the different marked sample images to the user along with one of the fetal heart images includes presenting in a specific order.

18. The imaging system of claim 17, wherein the processor executes an instruction that causes the computing system to perform operations including the one of the different marked sample images being sequentially presented to the user along with the one of the fetal heart images includes seven anatomical structures of the fetal heart in the order of:
1) aorta at a stomach level;
2) aorta at a level of a four-chamber view;
3) a crux at a level of the four-chamber view;
4) a right atrial wall at a level of the four-chamber view;
5) a pulmonary valve;
6) a superior vena cava; and
7) a transverse aortic arch.

19. The imaging system of claim 15, wherein the processor executes an instruction that causes the computing system to perform operations including prompting the user to mark three different features of one of the fetal heart images.

20. The imaging system of claim 19, wherein the one fetal heart image marked with the three different features includes markings of a location of an aorta, a location of a crux, and a location of a right atrial wall.

21. The imaging system of claim 15, wherein the processor executes an instruction that causes the computing system to perform operations including displaying the fetal echocardiography views of the fetal heart further includes displaying the fetal echocardiography views simultaneously in a single display to the user.

22. A method of examining fetal hearts and identifying normality or abnormality of fetal hearts, comprising:
obtaining spatiotemporal image correlation ultrasound data of a fetal heart to generate a plurality of fetal heart images at different cardiac phases;
presenting to a user a first sample heart image having a first location identified therein, the first location marking a location of a first structure in the first sample heart image;
presenting to the user a first fetal heart image from the plurality of fetal heart images that is selected based on the first sample heart image;
prompting the user to mark a location of the first structure on the first fetal heart image based on the marked first location in the first sample heart image;
presenting to the user a second sample heart image having a second location identified therein, the second location marking a location of a second structure in the second sample heart image;
presenting to the user a second fetal heart image from the plurality of fetal heart images that is selected based on the second sample heart image;
prompting the user to mark a location of the second structure on the second fetal heart image based on the marked second location in the second sample heart image;
reconstructing a unique geometric model of the fetal heart based on at least the marked first fetal heart image and based on the marked second fetal heart image, from which fetal echocardiography views can be extracted; and
displaying the fetal echocardiography views of the fetal heart.

23. The method of claim 22, further comprising presenting a total of seven sample heart images, which include the first sample heart image and the second sample heart image, and prompting the user for each of the seven sample heart images to mark locations of structures in fetal heart images based on the seven sample heart images, which include the first fetal heart image and the second fetal heart image, and reconstructing the unique geometric model of the fetal heart using the marked locations of the structures in the fetal heart images.

24. The method of claim 1, wherein the one fetal heart image presented to the user is selected based on the one of the different marked sample images presented to the user.

25. The imaging system of claim 15, wherein the one fetal heart image presented to the user is selected based on the one of the different marked sample images presented to the user.

26. The method of claim 1, wherein reconstructing the unique geometric model of the fetal heart further includes performing calculations required to reconstruct the heart in three dimensions by generating a mathematical reconstruction of the fetal heart.

27. The method of claim 26, wherein reconstructing the unique geometric model of the fetal heart is based on inferences of anatomical relationships in multiple dimensions that are not dependent on a pre-determined model of the fetal heart.

28. The machine readable medium that includes the instruction set of claim 8, wherein reconstructing the unique geometric model of the fetal heart further includes performing calculations required to reconstruct the heart in three dimensions by generating a mathematical reconstruction of the fetal heart.

29. The machine readable medium that includes the instruction set of claim 28, wherein reconstructing the unique geometric model of the fetal heart is based on inferences of anatomical relationships in multiple dimensions that are not dependent on a pre-determined model of the fetal heart.

30. The imaging system of claim 15, wherein reconstructing the unique geometric model of the fetal heart further includes performing calculations required to reconstruct the heart in three dimensions by generating a mathematical reconstruction of the fetal heart.

31. The imaging system of claim 30, wherein reconstructing the unique geometric model of the fetal heart is based on inferences of anatomical relationships in multiple dimensions that are not dependent on a pre-determined model of the fetal heart.

32. The method of claim 22, wherein reconstructing the unique geometric model of the fetal heart further includes performing calculations required to reconstruct the heart in three dimensions by generating a mathematical reconstruction of the fetal heart.

33. The method of claim 32, wherein reconstructing the unique geometric model of the fetal heart is based on inferences of anatomical relationships in multiple dimensions that are not dependent on a pre-determined model of the fetal heart.

* * * * *